(12) United States Patent
Broggini

(10) Patent No.: US 11,684,620 B2
(45) Date of Patent: *Jun. 27, 2023

(54) PHARMACEUTICAL COMPOSITIONS COMPRISING N-(3,5-DIMETHOXYPHENYL)-N'-(1-METHYLETHYL)-N-[3-(1-METHYL-1H-PYRAZOL-4-YL)QUINOXALIN-6-YL]ETHANE-1,2-DIAMINE

(71) Applicant: ASTEX THERAPEUTICS LTD, Cambridge (GB)

(72) Inventor: Diego Fernando Domenico Broggini, Schaffhausen (CH)

(73) Assignee: ASTEX THERAPEUTICS LTD, Cambridge (GB)

( * ) Notice: Subject to any disclaimer, the term of this patent is extended or adjusted under 35 U.S.C. 154(b) by 252 days.

This patent is subject to a terminal disclaimer.

(21) Appl. No.: 17/125,261

(22) Filed: Dec. 17, 2020

(65) Prior Publication Data

US 2021/0169877 A1    Jun. 10, 2021

Related U.S. Application Data

(63) Continuation of application No. 15/549,881, filed as application No. PCT/EP2016/052743 on Feb. 9, 2016, now Pat. No. 10,898,482.

(30) Foreign Application Priority Data

Feb. 10, 2015  (EP) ..................... 15154554
Oct. 8, 2015   (EP) ..................... 15188982

(51) Int. Cl.
| | | |
|---|---|---|
| A61K 31/498 | (2006.01) | |
| A61K 47/26  | (2006.01) | |
| A61K 47/18  | (2017.01) | |
| A61K 9/20   | (2006.01) | |
| A61K 9/48   | (2006.01) | |
| C09K 15/20  | (2006.01) | |

(52) U.S. Cl.
CPC .......... *A61K 31/498* (2013.01); *A61K 9/2018* (2013.01); *A61K 9/2054* (2013.01); *A61K 9/4858* (2013.01); *A61K 47/18* (2013.01); *A61K 47/26* (2013.01); *C09K 15/20* (2013.01)

(58) Field of Classification Search
CPC ...... A61K 31/498; A61K 47/18; A61K 47/26; C09K 15/20
See application file for complete search history.

(56) References Cited

U.S. PATENT DOCUMENTS

| | | | |
|---|---|---|---|
| 2,940,972 A | 6/1960 | Roch | |
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |
| 5,457,105 A | 10/1995 | Barker | |
| 5,700,823 A | 12/1997 | Hirth et al. | |
| 5,710,158 A | 1/1998 | Myers et al. | |
| 5,733,913 A | 3/1998 | Blankley et al. | |
| 5,882,864 A | 3/1999 | An et al. | |
| 6,060,498 A | 5/2000 | Ashizawa et al. | |
| 6,218,529 B1 | 4/2001 | An et al. | |
| 6,271,231 B1 | 8/2001 | Bergstrand et al. | |
| 6,331,555 B1 | 12/2001 | Hirth et al. | |
| 7,135,311 B1 | 11/2006 | David et al. | |
| 7,432,279 B2 | 10/2008 | Green et al. | |
| 8,628,796 B2 | 1/2014 | Kottayil et al. | |
| 8,895,601 B2 | 11/2014 | Saxty et al. | |
| 9,145,367 B2 | 9/2015 | Tazi et al. | |
| 9,221,804 B2 | 12/2015 | Leonard et al. | |
| 9,290,478 B2 | 3/2016 | Saxty et al. | |
| 9,303,029 B2 | 4/2016 | Woodhead et al. | |
| 9,303,030 B2 | 4/2016 | Angibaud et al. | |
| 9,309,241 B2 | 4/2016 | Angibaud et al. | |
| 9,309,242 B2 | 4/2016 | Berdini et al. | |
| 9,439,896 B2 | 9/2016 | Berdini et al. | |
| 9,447,098 B2 | 9/2016 | Saxty et al. | |
| 9,464,071 B2 | 10/2016 | Saxty et al. | |
| 9,493,426 B2 | 11/2016 | Angibaud et al. | |
| 9,527,844 B2 | 12/2016 | Angibaud et al. | |
| 9,737,544 B2 | 8/2017 | Angibaud et al. | |
| 9,757,364 B2 | 9/2017 | Angibaud et al. | |
| 9,850,228 B2 | 12/2017 | Saxty et al. | |
| 9,856,236 B2 | 1/2018 | Saxty et al. | |
| 9,902,714 B2 | 2/2018 | Vermeulen | |
| 10,039,759 B2 | 8/2018 | Berdini et al. | |

(Continued)

FOREIGN PATENT DOCUMENTS

| | | |
|---|---|---|
| CA | 2502825 A1 | 5/2004 |
| CA | 2524525 | 12/2004 |

(Continued)

OTHER PUBLICATIONS

International Search Report for PCT/EP2016/052743 dated May 20, 2016.

(Continued)

*Primary Examiner* — Theodore R. Howell
(74) *Attorney, Agent, or Firm* — Heslin Rothenberg Farley & Mesiti P.C.

(57) ABSTRACT

The invention relates to pharmaceutical compositions comprising N-(3,5-dimethoxyphenyl)-N'-(1-methylethyl)-N-[3-(1-methyl-1H-pyrazol-4-yl)quinoxalin-6-yl]ethane-1,2-diamine, or a pharmaceutically acceptable salt thereof or a solvate thereof; to processes for the preparation of said compositions and to the use of said compositions for the manufacture of a medicament for the prophylaxis of or the treatment, in particular the treatment, of diseases, e.g. cancer.

87 Claims, 2 Drawing Sheets

(56) References Cited

U.S. PATENT DOCUMENTS

Figure 1:
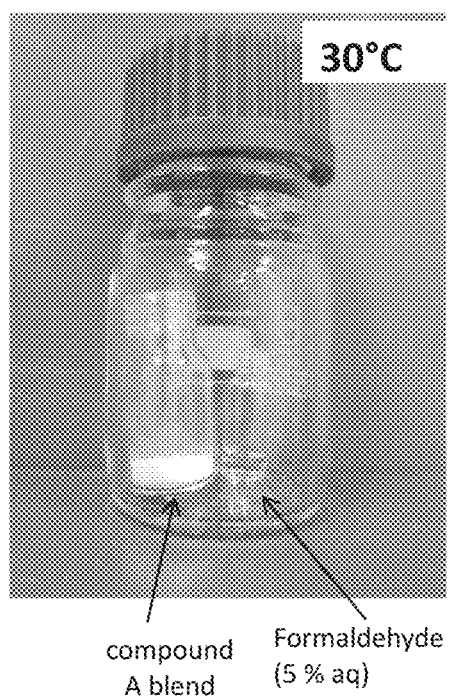

| | | |
|---|---|---|
| 10,045,982 B2 | 8/2018 | Berdini et al. |
| 10,052,320 B2 | 8/2018 | Woodhead et al. |
| 10,085,982 B2 | 10/2018 | Jovcheva et al. |
| 10,272,087 B2 | 4/2019 | Saxty et al. |
| 10,421,747 B2 | 9/2019 | Vermeulen et al. |
| 10,478,494 B2 | 11/2019 | Karkera et al. |
| 10,519,137 B2 | 12/2019 | Saxty et al. |
| 10,716,787 B2 | 7/2020 | Jovcheva et al. |
| 10,736,900 B2 | 8/2020 | Jovcheva et al. |
| 10,898,482 B2 | 1/2021 | Broggini |
| 2003/0207886 A1 | 11/2003 | Plücker et al. |
| 2003/0229067 A1 | 12/2003 | Castelhano et al. |
| 2003/0235628 A1 | 12/2003 | Taneja et al. |
| 2004/0204450 A1 | 10/2004 | Bechle et al. |
| 2005/0261307 A1 | 11/2005 | Cai et al. |
| 2005/0272727 A1 | 12/2005 | Dong et al. |
| 2005/0272728 A1 | 12/2005 | Altenbach et al. |
| 2005/0272736 A1 | 12/2005 | Altenbach et al. |
| 2006/0188568 A1 | 8/2006 | Bhamare et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0117097 A1 | 5/2009 | Igawa et al. |
| 2009/0118261 A1 | 5/2009 | Aquila et al. |
| 2009/0162352 A1 | 6/2009 | Adler et al. |
| 2009/0208575 A1 | 8/2009 | Gunupati et al. |
| 2009/0221591 A1 | 9/2009 | Hartmann et al. |
| 2009/0263397 A1 | 10/2009 | Buck et al. |
| 2010/0228026 A1 | 9/2010 | Yoshida et al. |
| 2010/0234347 A1 | 9/2010 | Dollinger et al. |
| 2011/0123545 A1 | 5/2011 | Marsh et al. |
| 2012/0172427 A1 | 7/2012 | Hauck |
| 2012/0302572 A1 | 11/2012 | Kan et al. |
| 2013/0072457 A1 | 3/2013 | Saxty et al. |
| 2013/0096021 A1 | 4/2013 | Chinnaiyan et al. |
| 2013/0267525 A1 | 10/2013 | Saxty et al. |
| 2013/0296326 A1 | 11/2013 | Pollock |
| 2014/0037642 A1 | 2/2014 | McCaffery et al. |
| 2014/0128430 A1 | 5/2014 | Frenkel et al. |
| 2014/0288053 A1 | 9/2014 | Berdini et al. |
| 2014/0296236 A1 | 10/2014 | Berdini et al. |
| 2015/0017637 A1 | 1/2015 | Chinnaiyan et al. |
| 2015/0031669 A1 | 1/2015 | Woodhead et al. |
| 2015/0031703 A1 | 1/2015 | Suzuki et al. |
| 2015/0057293 A1 | 2/2015 | Angibaud et al. |
| 2015/0105368 A1 | 4/2015 | Saxty et al. |
| 2015/0191791 A1 | 7/2015 | Shibata |
| 2015/0203589 A1 | 7/2015 | Iavarone et al. |
| 2015/0239883 A1 | 8/2015 | Angibaud et al. |
| 2015/0291589 A1 | 10/2015 | Saxty et al. |
| 2015/0307945 A1 | 10/2015 | Nakanishi et al. |
| 2016/0031856 A1 | 2/2016 | Saxty et al. |
| 2016/0075666 A1 | 3/2016 | Angibaud et al. |
| 2016/0090633 A1 | 3/2016 | Platero et al. |
| 2016/0108034 A1 | 4/2016 | Angibaud et al. |
| 2016/0213677 A1 | 7/2016 | Angibaud et al. |
| 2016/0220564 A1 | 8/2016 | Woodhead et al. |
| 2016/0235744 A1 | 8/2016 | Berdini et al. |
| 2016/0287699 A1 | 10/2016 | Karkera et al. |
| 2016/0311800 A1 | 10/2016 | Saxty et al. |
| 2017/0000781 A1 | 1/2017 | Berdini et al. |
| 2017/0000796 A1 | 1/2017 | Saxty et al. |
| 2017/0100406 A1 | 4/2017 | Jovcheva et al. |
| 2017/0101396 A1 | 4/2017 | Vermeulen et al. |
| 2017/0105978 A1 | 4/2017 | Angibaud et al. |
| 2017/0119763 A1 | 5/2017 | Jovcheva et al. |
| 2018/0021332 A1 | 1/2018 | Broggini |
| 2018/0127397 A1 | 5/2018 | Saxty et al. |
| 2018/0186775 A1 | 7/2018 | Vermeulen et al. |
| 2018/0296558 A1 | 10/2018 | Jovcheva et al. |
| 2020/0108141 A1 | 4/2020 | Karkera et al. |
| 2020/0131153 A1 | 4/2020 | Saxty et al. |
| 2021/0038598 A1 | 2/2021 | Jovcheva et al. |
| 2022/0135544 A1 | 5/2022 | Saxty et al. |

FOREIGN PATENT DOCUMENTS

| | | |
|---|---|---|
| CA | 2524948 | 12/2004 |
| CN | 1128496A A | 8/1996 |
| CN | 1966500 A | 5/2007 |
| CN | 102036963 A | 4/2011 |
| CN | 105030777 A | 11/2015 |
| CN | 105147687 A | 12/2015 |
| EP | 0544445 A2 | 6/1993 |
| EP | 1001946 | 5/2000 |
| EP | 1659175 A1 | 5/2006 |
| EP | 1208231 B1 | 1/2007 |
| EP | 1964837 A1 | 9/2008 |
| EP | 1990342 | 11/2008 |
| EP | 2332939 | 6/2011 |
| EP | 2650293 A1 | 10/2013 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 94/26723 A2 | 11/1994 |
| WO | 95/19169 A2 | 7/1995 |
| WO | 98/54156 A1 | 12/1998 |
| WO | 9909845 A1 | 3/1999 |
| WO | 99/17759 A2 | 4/1999 |
| WO | 99/42463 A1 | 8/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 03/055491 A1 | 7/2003 |
| WO | 03/086394 A1 | 10/2003 |
| WO | 2004/006355 A2 | 1/2004 |
| WO | 2004/011465 A1 | 2/2004 |
| WO | 2004/030635 A2 | 4/2004 |
| WO | 2004/043950 A1 | 5/2004 |
| WO | 2004/056822 A1 | 7/2004 |
| WO | 2004065378 A1 | 8/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/012288 A1 | 2/2005 |
| WO | 2005/039587 A1 | 5/2005 |
| WO | 2005/047244 A2 | 5/2005 |
| WO | 2005/054201 A1 | 6/2005 |
| WO | 2005054231 A1 | 6/2005 |
| WO | 2005/061463 A1 | 7/2005 |
| WO | 2006/040052 A1 | 4/2006 |
| WO | 2006040568 A1 | 4/2006 |
| WO | 2006/066361 A1 | 6/2006 |
| WO | 2006084338 A1 | 8/2006 |
| WO | 2006/092430 A1 | 9/2006 |
| WO | 2006/120456 A1 | 11/2006 |
| WO | 2006124354 A2 | 11/2006 |
| WO | 2007/003419 A1 | 1/2007 |
| WO | 2007/023186 A1 | 3/2007 |
| WO | 2007/044729 A2 | 4/2007 |
| WO | 2007054556 A1 | 5/2007 |
| WO | 2007/075567 A1 | 7/2007 |
| WO | 2007/117607 A2 | 10/2007 |
| WO | 2007/125405 A2 | 11/2007 |
| WO | 2007/132227 A1 | 11/2007 |
| WO | 2007140222 A2 | 12/2007 |
| WO | 2008/003702 A2 | 1/2008 |
| WO | 2008/021389 A2 | 2/2008 |
| WO | 2008/060907 A2 | 5/2008 |
| WO | 2008/076278 A1 | 6/2008 |
| WO | 2008/078091 A1 | 7/2008 |
| WO | 2008/082198 A1 | 7/2008 |
| WO | 2008079988 A2 | 7/2008 |
| WO | 2008080015 A2 | 7/2008 |
| WO | 2008109465 A2 | 9/2008 |
| WO | 2008112408 A1 | 9/2008 |
| WO | 2008/138878 A2 | 11/2008 |
| WO | 2008/141065 A1 | 11/2008 |

(56) References Cited

FOREIGN PATENT DOCUMENTS

| | | |
|---|---|---|
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009020990 A1 | 2/2009 |
| WO | 2009/064835 A1 | 5/2009 |
| WO | 2009/137378 A1 | 11/2009 |
| WO | 2009/141386 A1 | 11/2009 |
| WO | 2010/056872 A2 | 5/2010 |
| WO | 2010059771 A1 | 5/2010 |
| WO | 2010/084152 A1 | 7/2010 |
| WO | 2010088177 A1 | 8/2010 |
| WO | 2010129570 A1 | 11/2010 |
| WO | 2010/138661 A1 | 12/2010 |
| WO | 2011/026579 A1 | 3/2011 |
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |
| WO | 2012/106556 A2 | 8/2012 |
| WO | 2012/118492 A1 | 9/2012 |
| WO | 2012/148540 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013076186 A1 | 5/2013 |
| WO | 2013087725 A1 | 6/2013 |
| WO | 2013089882 A2 | 6/2013 |
| WO | 2013133351 A1 | 9/2013 |
| WO | 2013173485 A1 | 11/2013 |
| WO | 2013/179033 A1 | 12/2013 |
| WO | 2013/179034 A1 | 12/2013 |
| WO | 2014/011672 A1 | 1/2014 |
| WO | 2014007369 A1 | 1/2014 |
| WO | 2014018673 A2 | 1/2014 |
| WO | 2014018841 A1 | 1/2014 |
| WO | 2014051022 A1 | 4/2014 |
| WO | 2014071419 A2 | 5/2014 |
| WO | 2014113729 A2 | 7/2014 |
| WO | 2014/174307 A1 | 10/2014 |
| WO | 2014165710 A2 | 10/2014 |
| WO | 2014/198337 A1 | 12/2014 |
| WO | 2014/201111 A1 | 12/2014 |
| WO | 2014193229 A2 | 12/2014 |
| WO | 2015017607 A2 | 2/2015 |
| WO | 2015144803 A1 | 10/2015 |
| WO | 2015144804 A1 | 10/2015 |
| WO | 2015144808 A1 | 10/2015 |
| WO | 2016048833 A2 | 3/2016 |
| WO | 2016128411 A1 | 8/2016 |
| WO | 2016134234 A1 | 8/2016 |
| WO | 2016/161239 A1 | 10/2016 |
| WO | 2018/220206 A1 | 12/2018 |

OTHER PUBLICATIONS

Extended European Search Report for European Application No. 15188982.1 dated Nov. 19, 2015.
Yan, L., et al. "An efficient synthesis of quinoxaline derivatives from 4-chloro-4-deoxy-α-D-galactose and their cytotoxic activities", Bioorganic & Medicinal Chemistry Letters, vol. 17, No. 3, 2006, pp. 609-612.
Thompson, A.M., et al. "Synthesis and Structure—Activity Relationships of 7-Substituted 3-(2,6-Dichlorophenyl)-1,6-napthyridin-2(1H)-ones as Selective Inhibitors of $pp60^{c-src}$", Journal of Medicinal Chemistry, vol. 43, No. 16, 2000, pp. 3134-3147.
Berge, S. M., et al. "Pharmaceutical Salts", Journal of Pharmaceutical Sciences, vol. 66, No. 1, 1977, pp. 1-19.
Deady, L. W. "Ring Nitrogen Oxidation of Amino Substituted Nitrogen Heterocycles with m-Chloroperbenzoic Acid", Synthetic Communications, vol. 7(8), 1977, pp. 509-514.
Knights, V., et al. "De-regulated FGF receptors as therapeutic targets in cancer", Pharmacology & Therapeutics, 2010; vol. 125(1), pp. 105-117.
Korc, M., et al. "The Role of Fibroblast Growth Factors in Tumor Growth", Current Cancer Drug Targets, vol. 9(5), 2009, pp. 639-651.
Angerer, L. M., et al. "Demonstration of Tissue-Specific Gene Expression by in Situ Hybridization", Methods in Enzymology, vol. 152, 1987, pp. 649-661.
Deprimo, S.E., et al. "Expression profiling of blood samples from an SU5416 Phase III metastatic colorectal cancer clinical trial: a novel strategy for biomarker identification", BMC Cancer, vol. 3, 2003; pp. 1-12.
Orre, M., et al., "VEGF, VEGFR-1, VEGFR-2, Microvessel Density and Endothelial Cell Proliferation in Tumours of the Ovary", Int. J. Cancer (Pred. Oncol.), vol. 84(2), 1999, pp. 101-108.
Zhou, Wenjun et al., "A Structure-Guided Approach to Creating Covalent FGFR Inhibitors", Chemistry & Biology, vol. 17, pp. 285-295 (2010).
Avendaño, C., et al., "Drugs That Inhibit Signalling Pathways for Tumor Cell Growth and Proliferation", Medicinal Chemistry of Anticancer Drugs, pp. 251-305 (2008).
Garuti, L., et al., Irreversible Protein Kinase Inhibitors, Current Medicinal Chemistry, vol. 18, No. 20, Jul. 1, 2011, pp. 2981-2994.
Vippagunta, S.R. et al., "Crystalline Solids", Advanced Drug Delivery Reviews, vol. 48, pp. 3-26 (2001).
Jordan, V.C., "Tamoxifen: A Most Unlikely Pioneering Medicine", Nature Reviews: Drug Discovery, vol. 2, pp. 205-213 (2003).
Hackam, D.G., et al., "Translation of Research Evidence From Animals to Humans", JAMA, vol. 14, pp. 1731-1732 (2006).
"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).
V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).
"Himicheskaja jenciklopedija" tom. 1, stranicy 242-243, izdatel'stvo "Sovetska jajencklopedija", Moskva, 1988 (In English: Chemical Encyclopedia (thesaurus), vol. 1, pp. 242-243, publishing house "Soviet encyclopedia", Moscow, 1988).
Dorwald, F.Z., "Side Reactions in Organic Synthesis: A Guide to Successfiil Synthesis Design", Weinheim:Wiley-VCH Verlag GmbH & Co. KGaA, 2005, ISBN: 3-527-31021.5.
Lima, L.M., et al., "Bioisosterism: A Usefiil Strategy for Molecular Modification and Drug Design", Current Medical Chemistry, vol. 12(1), pp. 23-49 (2005).
Patani, G.A., et al., "Bioisosterism: A Rational Approach in Dmg Design", Chem. Rev. vol. 96, pp. 3147-3176 (1996).
Dieci, M. V., et al., Fibroblast Growth Factor Receptor Inhibitors as a Cancer Treatment: From a Biologic Rationale to Medical Perspectives, Cancer Discovery, vol. 3, No. 3, pp. 264-279 (Feb. 2013).
Gallick, G.E., et al., Small-molecule protein tyrosine kinase inhibitors for the treatment of metastatic prostate cancer, Future Medicinal Chemistry, vol. 4, No. 1, pp. 107-119 (Jan. 2012).
Study to Assess the Relative Bioavailability of Orally Administered JNJ-42756493 Tablet Versus JNJ-42756493 Capsule in Healthy Participants, ClinicalTrials.gov, pp. 1-4 (2014).
Matsuda, Y., et al., Fibroblast Growth Factor Receptor-2 IIIc as a Novel Molecular Target in Colorectal Cancer, Current Colorectal Cancer Reports, vol. 10, No. 1, pp. 20-26 (2014).

(56) References Cited

OTHER PUBLICATIONS

Carneiro, B.A., et al., Emerging therapeutic targets in bladder cancer, *Cancer Treatment Reviews*, vol. 41, No. 2, pp. 170-178 (2015).
Fujita, M., et al., Generation of Formaldehyde by Pharmaceutical Excipients and Its Absorption by Meglumine, *Chem. Pharm. Bull*, vol. 57, No. 10, pp. 1096-1099 (2009).
Adcock, J., et al., Diversity oriented synthesis: substitution at C5 in unreactive pyrimidines by Claisen rearrangement and reactivity in nucleophilic substitution at C2 and C4 in pteridines and pyrido[2,3-d]pyrmidines, *Tetrahedron*, vol. 67, pp. 3226-3237 (2011).
Database Caplus, Grina, et al., Preparation of oxohydroquinazolinylaminophenylpropanesulfonamide derivatives and analogs for use as Raf inhibitors, Document No. 157:465574, Accession No. 2012:1301209 (2012).
Liang, G., et al., "Small molecule inhibition of fibroblast growth factor receptors in cancer", *Cytokine & Growth Factor Reviews*, vol. 24, pp. 467-475 (2013).
Golub, T.R., et al., "Molecular Classification of Cancer: Class Discovery and Class Prediction by Gene Expression Monitoring", *Science*, vol. 286, pp. 531-537 (1999).
Greulich, H., et al., "Targeting mutant fibroblast growth factor receptors in cancer", *Trends in Molecular Medicine*, vol. 17, No. 5, pp. 283-292 (2011).
Freshney, R.I., "Culture of Animal Cells, A Manual of Basic Technique", Published by Alan R. Liss, Inc, New York, pp. 1-6 (1983).
Cohen, P., "The development and therapeutic potential of protein kinase inhibitors", *Current Opinion in Chemical Biology*, vol. 3, pp. 459-465 (1999).
Cecil Textbook of Medicine, edited by Bennet, J.C., and Plum, F., 20th edition, vol. 1, pp. 1004-1010 (1996).
Hynes, N.E., et al., "Potential for Targeting the Fibroblast Growth Factor Receptors in Breast Cancer", *Cancer Research*, vol. 70, pp. 5199-5202 (2010).
Neidle, S., "Cancer Drug Design and Discovery", Elsevier/Academic Press, pp. 427-431 (2008).
Dermer, G.B., "Another Anniversary for the War on Cancer", *Biotechnology*, vol. 12, p. 320 (1994).
Katoh, Y., et al., "FGFR2-related pathogenesis and FGFR2-targeted therapeutics (Review)", *International Journal of Molecular Medicine*, vol. 23, pp. 307-311 (2009).
Jain, V.K., et al., "Challenges and opportunities in the targeting of fibroblast growth factor receptors in breast cancer", *Breast Cancer Research*, vol. 14, No. 208, pp. 1-9 (2012).
Ho, H.K., et al., "Current strategies for inhibiting FGFR activities in clinical applications: opportunities, challenges and toxicological considerations", *Drug Discovery Today*, vol. 19, Issue 1, pp. 51-62 (2014).
Sonpavde, G., et al., "Fibroblast growth factor receptors as therapeutic targets in clear-cell renal cell carcinoma", *Expert Opinion on Investigational Drugs*, vol. 23, Issue 3, pp. 305-315 (2014).
Rodriguez-Vida, A., et al., "Complexity of FGFR signaling in metastatic urothelial cancer", *Journal of Hematology & Oncology*, vol. 8, pp. 119 et seq. (2015).
D.A.Kharkevich, Farmakologiya (Pharmacology), 1996, M., Meditsina, p. 41, chapter 6.A (in Russian Only).
V.G.Belikov, Farmatsevticheskaya khimiya (Pharmaceutical Chemistry), M., Vysshaya shkola, 1993, p. 1, chapter 2.2, pp. 43-47) (in Russian only).
Dienstmann et al., "Genomic Aberrations in the FGFR Pathway: Opportumties for Targeted Therapies in Solid Tumors," Annals of Oncology, vol. 25, Nov. 20, 2013, No. 3, pp. 552-563.
Parker et al., "Emergence of FGFR Family Gene Fusions as Therapeutic Targets in a Wide Spectrum of Solid Tumours," Journal of Pathology, Oct. 29, 2013, vol. 232, No. 1, pp. 4-15.
Arai et al., "Fibroblast Growth Factor Receptor 2 Tyrosine Kinase Fusions Define a Unique Molecular Subtype of Cholangiocarcinoma," Hepatology, Apr. 2014, vol. 59, No. 4, pp. 1427-1434.

Bahleda et al., "Phase 1 Study of JNJ-42756493, a Pan-Fibroblast Growth Factor Receptor (FGFR) Inhibitor, in Patients with Advanced Solid Tumors," Journal of Clinical Oncology, May 2014, vol. 32, No. 15, pp. 2501-2501.
Di Stefano et al., "Detection, Characterization, and Inhibition of FGFR-TACC Fusions in IDH Wild-Type Glioma," Clinical Cancer Research, Jan. 21, 2015, vol. 21, No. 14, pp. 3307-3317.
Parker, B.C., et al., "The tumorigenic FGFR3-TACC3 gene fusion escapes miR-99a regulation in glioblastoma," *The Journal of Clinical Investigation*, 123 (2), pp. 855-865, Feb. 1, 2013.
Bello, et al., "E=3810 is a Potent Dual Inhibitor of VEGFR and FGFR that Exerts Antitumor Activity in Multiple Preclinical Models," vol. 71(4), pp. 1396-1405 (2011).
Database, Geneseq [Online], "FGFR3-TACC3 gene fusion PCR primer, FGFR3-TACC3(F18T11)_qPCR_F SEQ: 15," XP002753027, Database accession No. BAT14432 (2013).
Database, Geneseq [Online], "Human FGFR 2 mRNA target sequence for mdRNA, SEQ ID:3954," XP055257043, Database accession No. ATM46802 (2008).
Gavine, et al., "AZD4547: An Orally Bioavailable, Potent, and Selective Inhibitor of the Fibroblast Growth Factor Receptor Tyrosine Kinase Family," *Cancer Research*, vol. 72(8), pp. 2045-2056 (2012).
International Search Report from PCT/US2015/050996 dated Mar. 23, 2016.
Mengual, et al., BMC Research Notes 1:21, pp. 1-8 (Jun. 2008).
Millholland, et al., Research and Reports in Urology, 4: 33-40 (2012).
Sabnis, et al., "FGFR Fusions in the Driver's Seat," *Cancer Discovery*, vol. 3 (6), pp. 607-609 (2013).
Shinmura, et al., "A novel somatic FGFR3 mutation in primary lung cancer," *Oncology Reports*, vol. 31 (3), pp. 1219-1224 (2014).
Singh, et al., "Transforming Fusions of FGFR and TACC Genes in Human Glioblastoma," *Science*, vol. 337 (6099), pp. 1231-1235 (2012).
Trudel, et al., "Evaluation of XL999, a Potent Inhibitor of FGFR3, for the Potential Treatment of t(4;14) Positive Multiple Myeloma," *Blood*, vol. 110 (11), pp. 741A-742A (2007).
Williams, et al., "Oncogenic FGFR3 gene fusions in bladder cancer," *Human Molecular Genetics*, vol. 22 (4), pp. 795-803 (2013).
Wu, et al., "Identification of Targetable FGFR Gene Fusions in Diverse Cancers," *Cancer Discovery*, vol. 3 (6), pp. 636-647 (2013).
Fujita, Megumi et al., "Stabilization by Meglumine of an Amine Compound Degraded by Formaldehyde in Tablets." International Journal of Pharmaceutics 386.1-2 (2010): 195-200.
Singleton, KR et al., "A Receptor Tyrosine Kinase Network Composed of Fibroblast Growth Factor Receptors, Epidermal Growth Factor Receptor, v-erb-b2 Erythroblastic Leukemia Viral Oncogene Homolog 2, and Hepatocyte Growth Factor Receptor Drives Growth and Survival of Head and Neck Squamous Carcinoma Cell Lines", Molecular Pharmacology, Apr. 2013, vol. 83, No. 4, pp. 882-893.
European Search Report for EP Application No. 15154554.8 dated Jul. 14, 2015.
Bronte et al., "Nintedanib in NSCLC: Evidence to Date and Place in Therapy," Therapeutic Advances in Medical Oncology, 2016, vol. 8[3], pp. 188-197.
Katoh et al., "FGFR inhibitors: Effects on Cancer Cells, Tumor Microenvironment and Whole-Body Homeostasis (Review)," International Journal of Molecular Medicine 2016, 38(1), pp. 3-15.
Angibaud et al., "Discovery of JNJ-42756493, A Potent Fibroblast Growth Factor Receptor (FGFR) Inhibitor Using a Fragment Based Approach," AACR Minisymposium, Small Molecule Design and Optimization San Diego, CA, Apr. 8, 2014, 16 pp.
André, Fabrice et al., "Rationale for targeting fibroblast growth factor receptor signaling in breast cancer," Breast Cancer Research and Treatment, vol. 150 No. 1, 2015, pp. 1-8.
Paola Corona et al., "Synthesis of N-(5,7-diamino-3-phenylquinoxalin-2-yl)-3,4,5-substituted anilines and N-[4[(5,7-diamino-3-phenylquinoxalin-2-yl)amino]benzoyl]-L-glutamic acid diethyl ester; Evaluation of in vitro anti-cancer and anti-folate activities," European Journal of Medicinal Chemistry 43 (2008) 189-203.

(56) References Cited

OTHER PUBLICATIONS

Paola Corona et al., "Synthesis and in vitro antitumor activity of new quinoxaline derivatives," European Journal of Medicinal Chemistry 44 (2009) 1579-1591.

Andrew M. Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem. 2000, 43, 4200-4211.

James M. Hamby et al., "Structure-Activity Relationships for a Novel Series of Pyrido[2,3-d]pyrimidine Tyrosine Kinase Inhibitors," Journal of Medicinal Chemistry, 1997, vol. 40, No. 15, 2296-2303.

Nozomu Fuse et al., The development of c-Met inhibitor, treatment of cancer molecule targets, vol. 7, No. 2, pp. 111 to 116 (2009).

Degradation of compound A in powder blends comprising various concentrations of meglumine in a formaldehyde stress test

PHARMACEUTICAL COMPOSITIONS COMPRISING N-(3,5-DIMETHOXYPHENYL)-N'-(1-METHYLETHYL)-N-[3-(1-METHYL-1H-PYRAZOL-4-YL)QUINOXALIN-6-YL]ETHANE-1,2-DIAMINE

CROSS REFERENCE TO RELATED APPLICATIONS

This application is a continuation application of U.S. application Ser. No. 15/549,881, which is a national stage filing under section 371 of International Application No. PCT/EP2016/052743, filed on Feb. 9, 2016, and published on Aug. 18, 2016 as WO 2016/128411, which claims priority to European Application No. 15154554.8, filed on Feb. 10, 2015, and to European Application No. 15188982.1, filed on Oct. 8, 2015.

FIELD OF THE INVENTION

The invention relates to pharmaceutical compositions comprising N-(3,5-dimethoxyphenyl)-N'-(1-methylethyl)-N-[3-(1-methyl-1H-pyrazol-4-yl)quinoxalin-6-yl]ethane-1,2-diamine, or a pharmaceutically acceptable salt thereof or a solvate thereof; to processes for the preparation of said compositions and to the use of said compositions for the manufacture of a medicament for the prophylaxis of or the treatment, in particular the treatment, of diseases, e.g. cancer.

BACKGROUND OF THE INVENTION

N-(3,5-dimethoxyphenyl)-N'-(1-methylethyl)-N-[3-(1-methyl-1H-pyrazol-4-yl)quinoxalin-6-yl]ethane-1,2-diamine is described in WO2011/135376, which is incorporated herein by reference.

The chemical structure of N-(3,5-dimethoxyphenyl)-N'-(1-methylethyl)-N-[3-(1-methyl-1H-pyrazol-4-yl)quinoxalin-6-yl]ethane-1,2-diamine (compound A herein) is:

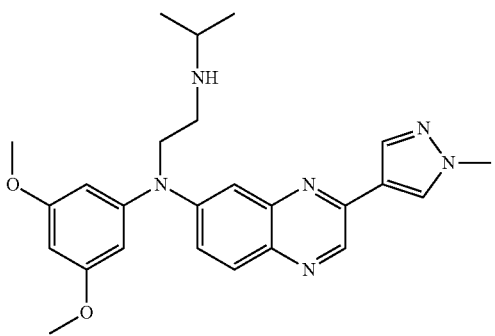 [SMILES: COc1cc(OC)cc(N(CCNC(C)C)c2ccc3ncc(-c4cnn(C)c4)nc3c2)c1]

SUMMARY OF THE INVENTION

According to an aspect of the invention there is provided a pharmaceutical composition comprising N-(3,5-dimethoxyphenyl)-N'-(1-methylethyl)-N-[3-(1-methyl-H-pyrazol-4-yl)quinoxalin-6-yl]ethane-1,2-diamine, a pharmaceutically acceptable salt thereof or a solvate thereof, a formaldehyde scavenger and a pharmaceutically acceptable carrier.

According to an aspect of the invention there is provided the use of a formaldehyde scavenger, in particular meglumine, to increase the stability, in particular the chemical stability, of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, in a pharmaceutical composition, in particular a solid pharmaceutical composition, in particular a capsule or a tablet.

FIGURES

FIG. 1: Experimental set-up of formaldehyde stress test in solid state (N-(3,5-dimethoxyphenyl)-N'-(1-methylethyl)-N-[3-(1-methyl-1H-pyrazol-4-yl)quinoxalin-6-yl]ethane-1,2-diamine=compound A)

Figure 2:
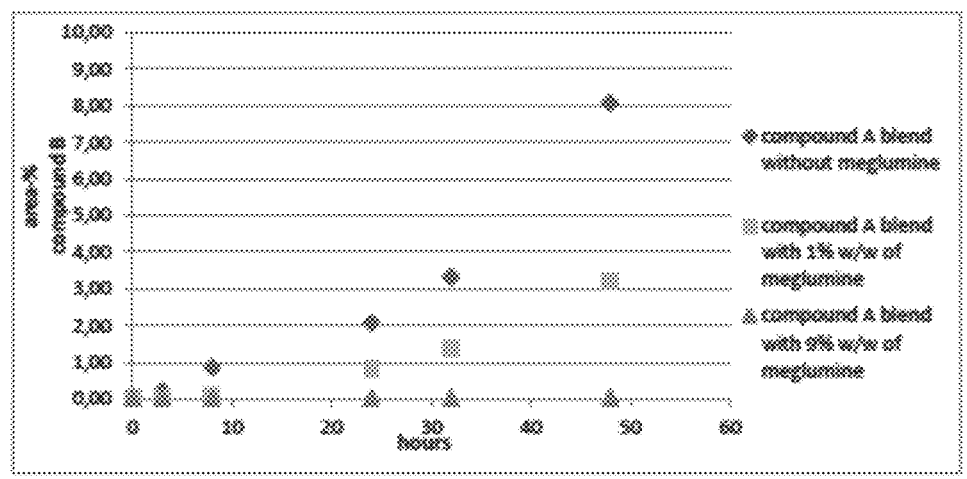

FIG. 2: Degradation of N-(3,5-dimethoxyphenyl)-N'-(1-methylethyl)-N-[3-(1-methyl-1H-pyrazol-4-yl)quinoxalin-6-yl]ethane-1,2-diamine (compound A) in powder blends comprising various concentrations of meglumine in a formaldehyde stress test: ◆ represents a starting powder blend of 2% w/w of compound A, mannitol, ■ microcrystalline cellulose, croscarmellose sodium and magnesium stearate; represents a starting powder blend of 2% w/w of compound A, 1% w/w of meglumine, mannitol, microcrystalline cellulose, croscarmellose sodium and magnesium stearate; ▲ represents a starting powder blend of 2% w/w of compound A, 9% w/w of meglumine, mannitol, microcrystalline cellulose, croscarmellose sodium and magnesium stearate. Compound B is 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine.

DETAILED DESCRIPTION OF THE INVENTION

It was found that N-(3,5-dimethoxyphenyl)-N'-(1-methylethyl)-N-[3-(1-methyl-1H-pyrazol-4-yl)quinoxalin-6-yl]ethane-1,2-diamine is sensitive to degradation, especially when incorporated in a solid pharmaceutical composition. In particular, N-(3,5-dimethoxyphenyl)-N'-(1-methylethyl)-N-[3-(1-methyl-1H-pyrazol-4-yl)quinoxalin-6-yl]ethane-1,2-diamine is sensitive, especially when incorporated in a solid pharmaceutical composition, to transformation into a cyclized product, 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine.

The chemical structure of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine (compound B herein) is.

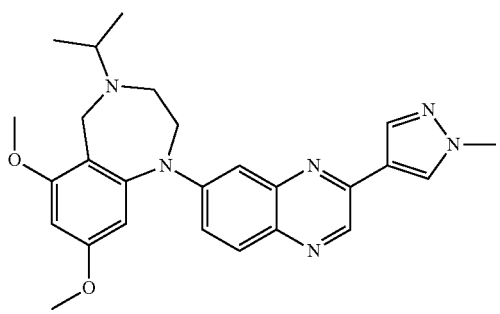 [SMILES: COc1cc(OC)c2c(c1)N(c1ccc3ncc(-c4cnn(C)c4)nc3c1)CCN(C(C)C)C2]

Without being bound to any theory, it seems the stability, in particular the chemical stability, of N-(3,5-dimethoxyphenyl)-N'-(1-methylethyl)-N-[3-(1-methyl-H-pyrazol-4-yl)

quinoxalin-6-yl]ethane-1,2-diamine is impaired by the effects of formaldehyde, and that 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine is formed by reaction of N-(3,5-dimethoxyphenyl)-N'-(1-methylethyl)-N-[3-(1-methyl-1H-pyrazol-4-yl)quinoxalin-6-yl]ethane-1,2-diamine with formaldehyde.

Formaldehyde can get in contact with N-(3,5-dimethoxyphenyl)-N'-(1-methylethyl)-N-[3-(1-methyl-1H-pyrazol-4-yl)quinoxalin-6-yl]ethane-1,2-diamine, from a variety of sources, such as for example from the environment, from other components or excipients present in the pharmaceutical composition comprising N-(3,5-dimethoxyphenyl)-N'-(1-methylethyl)-N-[3-(1-methyl-1H-pyrazol-4-yl)quinoxalin-6-yl]ethane-1,2-diamine, from the container or package comprising a pharmaceutical composition, in particular a solid pharmaceutical composition, comprising N-(3,5-dimethoxyphenyl)-N'-(1-methylethyl)-N-[3-(1-methyl-1H-pyrazol-4-yl)quinoxalin-6-yl]ethane-1,2-diamine.

Notwithstanding the fact that it was found that 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine exhibits FGFR inhibitory activity, it is still desirable for a pharmaceutical composition that the formation of byproducts is prevented, postponed, slowed down or diminished.

It was found that the stability, in particular the chemical stability, of N-(3,5-dimethoxyphenyl)-N'-(1-methylethyl)-N-[3-(1-methyl-1H-pyrazol-4-yl)quinoxalin-6-yl]ethane-1,2-diamine, in particular when incorporated in a solid pharmaceutical composition, such as for example a capsule or a tablet, could be increased by adding one or more formaldehyde scavengers. Without being bound to any theory, when incorporated in a pharmaceutical composition, in particular in a solid pharmaceutical composition, such as for example a capsule or a tablet, excipients and active ingredient are in close contact with each other and this can have an effect on the extent and/or rate of the transformation of N-(3,5-dimethoxyphenyl)-N'-(1-methylethyl)-N-[3-(1-methyl-1H-pyrazol-4-yl)quinoxalin-6-yl]ethane-1,2-diamine to 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine.

Thus the present invention provides for pharmaceutical compositions comprising as active pharmaceutical ingredient N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, with an improved stability or a longer shelf life. The shelf life of the compositions of the present invention is at least 12 months, at least 18 months, at least 24 months.

Formaldehyde scavengers are compounds that are capable of absorbing formaldehyde. They include compounds comprising a nitrogen center that is reactive with formaldehyde, such as to form one or more reversible or irreversible bonds between the formaldehyde scavenger and formaldehyde. For example, the formaldehyde scavenger comprises one or more nitrogen atoms/centers that are reactive with formaldehyde to form a schiff base imine that is capable of subsequently binding with formaldehyde. For example, the formaldehyde scavenger comprises one or more nitrogen centers that are reactive with formaldehyde to form one or more 5-8 membered cyclic rings. The formaldehyde scavenger preferably comprises one or more amine or amide groups. For example, the formaldehyde scavenger can be an amino acid, an amino sugar, an alpha amine compound, or a conjugate or derivative thereof, or a mixture thereof. The formaldehyde scavenger may comprise two or more amines and/or amides.

Formaldehyde scavengers include, for example, glycine, alanine, serine, threonine, cysteine, valine, lecuine, isoleucine, methionine, phenylalanine, tyrosine, aspartic acid, glutamic acid, arginine, lysine, ornithine, citrulline, taurine pyrrolysine, meglumine, histidine, aspartame, proline, tryptophan, citrulline, pyrrolysine, asparagine, glutamine, or a conjugate or mixture thereof; or, whenever possible, pharmaceutically acceptable salts thereof.

In an aspect of the invention, the formaldehyde scavenger is meglumine or a pharmaceutically acceptable salt thereof, in particular meglumine base.

An aspect of the invention is the use of a formaldehyde scavenger, in particular meglumine, in a pharmaceutical composition, in particular a solid pharmaceutical composition, in particular a capsule or a tablet, to increase the stability, in particular the chemical stability of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base contained in said composition. The stability, in particular chemical stability, is increased compared to a pharmaceutical composition containing no formaldehyde scavenger.

An aspect of the invention is a method of stabilizing N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, in a pharmaceutical composition, in particular a solid pharmaceutical composition, suchs as a capsule or a tablet, comprising adding a formaldehyde scavenger, in particular meglumine, to said composition.

An aspect of the invention is the use of a formaldehyde scavenger, in particular meglumine, in a pharmaceutical composition, in particular a solid pharmaceutical composition, such as a capsule or a tablet, to prevent, postpone, slow down or diminish the transformation of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, contained in the composition, into 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, a pharmaceutically acceptable salt thereof or a solvate thereof.

An aspect of the invention is the use of a formaldehyde scavenger, in particular meglumine, in a pharmaceutical composition, in particular a solid pharmaceutical composition, such as a capsule or a tablet, to prevent, postpone, slow down or diminish the transformation of N-(3,5-dimethoxyphenyl)-N'-(1-methylethyl)-N-[3-(1-methyl-1H-pyrazol-4-yl)quinoxalin-6-yl]ethane-1,2-diamine contained in the composition into 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine.

An aspect of the invention is a method of preventing, postponing, slowing down or diminishing the transformation of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof contained in a pharmaceutical composition, in particular a solid pharmaceutical composition, such as a capsule or a tablet, into 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, a pharmaceutically acceptable salt thereof or a solvate thereof, comprising adding a formaldehyde scavenger, in particular meglumine, to said composition.

An aspect of the invention is a method of preventing, postponing, slowing down or diminishing the transformation of N-(3,5-dimethoxyphenyl)-N'-(1-methylethyl)-N-[3-(1-methyl-1H-pyrazol-4-yl)quinoxalin-6-yl]ethane-1,2-diamine contained in a pharmaceutical composition, in particular a solid pharmaceutical composition, such as a capsule or a tablet, into 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, comprising adding a formaldehyde scavenger, in particular meglumine, to said composition.

An aspect of the invention is the use of a formaldehyde scavenger, in particular meglumine, in a pharmaceutical composition, in particular a solid pharmaceutical composition, in particular a capsule or a tablet, comprising N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, to prevent, postpone, slow down or diminish the formation of 6,8-dimethoxy-4-(1-methylethyl)-1-[3-(1-methyl-1H-pyrazol-4-yl)quinoxalin-6-yl]-2,3,4,5-tetrahydro-11H-1,4-benzodiazepine, a pharmaceutically acceptable salt thereof or a solvate thereof, in said composition.

An aspect of the invention is the use of a formaldehyde scavenger, in particular meglumine, in a pharmaceutical composition, in particular a solid pharmaceutical composition, in particular a capsule or a tablet, comprising N-(3,5-dimethoxyphenyl)-N'-(1-methylethyl)-N-[3-(1-methyl-1H-pyrazol-4-yl)quinoxalin-6-yl]ethane-1,2-diamine, to prevent, postpone, slow down or diminish the formation of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine in said composition.

An aspect of the invention is a pharmaceutical composition comprising N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof; a formaldehyde scavenger, in particular meglumine; and a pharmaceutically acceptable carrier; in particular a pharmaceutical composition comprising N-(3,5-dimethoxyphenyl)-N'-(1-methylethyl)-N-[3-(1-methyl-1H-pyrazol-4-yl)quinoxalin-6-yl]ethane-1,2-diamine; a formaldehyde scavenger, in particular meglumine; and a pharmaceutically acceptable carrier.

An aspect of the invention is a solid pharmaceutical composition, such as a capsule or a tablet, comprising N-(3,5-dimethoxyphenyl)-N'-(1-methylethyl)-N-[3-(1-methyl-H-pyrazol-4-yl)quinoxalin-6-yl]ethane-1,2-diamine, a pharmaceutically acceptable salt thereof or a solvate thereof; a formaldehyde scavenger, in particular meglumine; and a pharmaceutically acceptable carrier; in particular a solid pharmaceutical composition, such as a capsule or a tablet, comprising N-(3,5-dimethoxyphenyl)-N'-(1-methylethyl)-N-[3-(1-methyl-1H-pyrazol-4-yl)quinoxalin-6-yl]ethane-1,2-diamine; a formaldehyde scavenger, in particular meglumine; and a pharmaceutically acceptable carrier.

In an aspect of the invention, the pharmaceutical compositions as described herein, comprise from 0-4% w/w, or from 0-3% w/w, or form 0-2% w/w, or from 0-1.5% w/w, or from 0-1% w/w, or from 0-0.5% w/w, or from 0-0.1% w/w, or from 0-0.05% w/w of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, a pharmaceutically acceptable salt thereof or a solvate thereof, in particular from 0-4% w/w, or from 0-3% w/w, or form 0-2% w/w, or from 0-1.5% w/w, or from 0-1% w/w, or from 0-0.5% w/w, or from 0-0.1% w/w, or from 0-0.05% w/w of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine.

In an aspect of the invention, the pharmaceutical compositions as described herein are suitable for oral administration, such as capsules or tablets, a pharmaceutical composition in the form of a tablet in particular for oral administration being preferred.

In an aspect of the invention, the pharmaceutical compositions as described herein are suitable for rectal administration. The tablets of the invention can be produced by conventional tabletting techniques together with pharmaceutically acceptable excipients (pharmaceutically acceptable carrier) and with conventional tabletting machines. As known in the art, tablet blends may be dry-granulated or wet-granulated before tabletting. It will be appreciated that the person skilled in the art will be able to recognize the most appropriate way to manufacture the compositions of the present invention.

In order to facilitate the swallowing of such a pharmaceutical composition for oral administration by a mammal, in particular a human, it is advantageous to give the compositions, in particular tablets, an appropriate shape.

Tablets or capsules of the present invention may further be film-coated e.g. to improve taste, to provide ease of swallowing and an elegant appearance. Polymeric film-coating materials are known in the art. Preferred film coatings are water based film coatings opposed to solvent based film coatings because the latter may contain more traces of aldehydes. A preferred film-coating material is Opadry® II aqueous film coating system, e.g. Opadry® II 85F, such as Opadry® II 85F92209. Further preferred film coatings are water based film coatings that protects from environmental moisture, such as Readilycoat® (e.g. Readilycoat® D), AquaPolish® MS, Opadry® amb, Opadry® amb II, which are aqueous moisture barrier film coating systems. A preferred film-coating is Opadry® amb II, a high performance moisture barrier film coating which is a PVA-based immediate release system, without polyethylene glycol.

In tablets according to the invention, the film coat in terms of weight preferably accounts for about 4% (w/w) or less of the total tablet weight.

For capsules according to the present invention, hypromellose (HPMC) capsules are preferred over gelatin capsules.

In an aspect of the invention, the pharmaceutical compositions as described herein, in particular in the form of a capsule or a tablet, comprise a therapeutically effective amount of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof.

In an aspect of the invention, the pharmaceutical compositions as described herein, in particular in the form of a capsule or a tablet, comprise from 0.5 mg to 20 mg base equivalent, or from 2 mg to 20 mg base equivalent, or from 0.5 mg to 12 mg base equivalent, or from 2 mg to 12 mg base equivalent, or from 2 mg to 10 mg base equivalent, or from 2 mg to 6 mg base equivalent, or 2 mg base equivalent, 3 mg base equivalent, 4 mg base equivalent, 5 mg base equivalent, 6 mg base equivalent, 7 mg base equivalent, 8 mg base equivalent, 9 mg base equivalent, 10 mg base equivalent, 11 mg base equivalent or 12 mg base equivalent of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof. In particular, the pharmaceutical compositions as described herein comprise 3 mg base equivalent, 4 mg base equivalent or 5 mg base equivalent of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof.

In an aspect of the invention, the pharmaceutical compositions as described herein, in particular in the form of a capsule or a tablet, comprise from 0.5 mg to 20 mg, or from 2 mg to 20 mg, or from 0.5 mg to 12 mg, or from 2 mg to 12 mg, or from 2 mg to 10 mg, or from 2 mg to 6 mg, or 2 mg, 3 mg, 4 mg, 5 mg, 6 mg, 7 mg, 8 mg, 9 mg, 10 mg, 11 mg or 12 mg of N-(3,5-dimethoxyphenyl)-N'-(1-methylethyl)-N-[3-(1-methyl-1H-pyrazol-4-yl)quinoxalin-6-yl]ethane-1,2-diamine base. In particular, the pharmaceutical compositions as described herein comprise 3 mg, 4 mg or 5 mg of N-(3,5-dimethoxyphenyl)-N'-(1-methylethyl)-N-[3-(1-methyl-1H-pyrazol-4-yl)quinoxalin-6-yl]ethane-1,2-diamine base. In particular, the pharmaceutical compositions as described herein comprise 3 mg, 4 mg or 5 mg of N-(3,5-dimethoxyphenyl)-N'-(1-methylethyl)-N-[3-(1-methyl-1H-pyrazol-4-yl)quinoxalin-6-yl]ethane-1,2-diamine base and from about 0.5 to about 5% w/w, from about 0.5 to about 3% w/w, from about 0.5 to about 2% w/w, from about 0.5 to about 1.5% w/w, or from about 0.5 to about 1% w/w of a formaldehyde scavenger, in particular meglumine. In particular, the pharmaceutical compositions as described herein comprise 3 mg, 4 mg or 5 mg of N-(3,5-dimethoxyphenyl)-N'-(1-methylethyl)-N-[3-(1-methyl-1H-pyrazol-4-yl)quinoxalin-6-yl]ethane-1,2-diamine base and from about 0.5 to about 1.5% w/w or from about 0.5 to about 1% w/w of a formaldehyde scavenger, in particular meglumine. In an aspect of the invention, more than one, e.g. two, pharmaceutical compositions as described herein can be administered in order to obtain a desired dose, e.g. a daily dose.

An aspect of the invention is a pharmaceutical composition as described herein, comprising particles of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, wherein the particles have a $d^{50}$ of about 1500 μm, of about 1000 μm, of about 500 μm, of about 400 μm, of about 250 μm, of about 200 μm, of about 150 μm, of about 125 μm, of about 100 μm, of about 95 μm, of about 90 μm, of about 85 μm, of about 80 μm, of about 75 μm, of about 70 μm, of about 65 μm, of about 60 μm, of about 55 μm, of about 50 μm, of about 45 μm, of about 40 μm, of about 35 μm, of about 30 μm, of about 25 μm, of about 20 μm, of about 15 μm, of about 10 μm, of about 5 μm. Preferably, the particles have a $d^{50}$ of about 125 μm, of about 100 μm, of about 95 μm, of about 90 μm, of about 85 μm, of about 80 μm, of about 75 μm, of about 70 μm, of about 65 μm, of about 60 μm, of about 55 μm, of about 50 μm. An aspect of the invention is a pharmaceutical composition as described herein, comprising particles of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, wherein the particles have a $d^{50}$ falling in the range from 5 μm to 1500 μm, or from 5 μm to 1000 μm, or from 5 μm to 500 μm, or from 5 μm to 400 μm, or from 5 μm to 250 μm, or from 5 μm to 200 μm, or from 5 μm to 150 μm, or from 5 μm to 125 μm, or from 5 μm to 100 μm, or from 5 μm to 80 μm, or from 5 μm to 75 μm, or from 5 μm to 70 μm, or from 5 μm to 65 μm, or from 5 μm to 60 μm, or from 5 μm to 55 μm, or from 5 μm to 50 μm, or from 5 μm to 45 μm, or from 5 μm to 40 μm, or from 5 μm to 35 μm, or from 5 μm to 30 μm, or from 5 μm to 25 μm, or from 5 μm to 20 μm, from 5 μm to 15 μm, or from 5 μm to 10 μm, or the particles have a $d^{50}$ falling in the range from 50 μm to 125 μm, or from 50 μm to 100 μm or from 50 μm to 75 μm.

As used herein, the term $d^{50}$ has its conventional meaning as known to the person skilled in the art and can be measured by art-known particle size measuring techniques such as, for example, sedimentation field flow fractionation, photon correlation spectroscopy, laser diffraction or disk centrifugation. The $d^{50}$ mentioned herein may be related to volume weighted distributions of the particles. In that instance, by "a $d^{50}$ of 50 μm" it is meant that at least 50% of the particles has a particle size (by volume or diameter of an equivalent sphere) less than 50 μm. In a similar manner, the $d^{50}$ particle size may be related to number weighted distributions of the particles. In that instance, by "$d^{50}$ of 50 μm" it is meant that at least 50% of the number weighted of the particles has a particle size (by number) of less than 50 μm. In particular, the $d^{50}$ mentioned herein represents a volume weighted distribution of the particles, in particular measured on a Malvern Mastersizer 2000.

The particle size can be an important factor determining tabletting speed, ejection forces, flowability and therefore the manufacturability on a large scale of a particular composition, and the quality of the final product.

The amount of formaldehyde scavenger, in particular meglumine, in the pharmaceutical compositions according to the present invention may range from about 0.1 to about 10% w/w, about 0.1 to about 5% w/w, from about 0.1 to about 3% w/w, from about 0.1 to about 2% w/w, from about 0.1 to about 1.5% w/w, from about 0.1 to about 1% w/w, from about 0.5 to about 5% w/w, from about 0.5 to about 3% w/w, from about 0.5 to about 2% w/w, from about 0.5 to about 1.5% w/w, from about 0.5 to about 1% w/w.

The pharmaceutical compositions of the invention, in particular capsules and/or tablets, may include one or more pharmaceutically acceptable excipients (pharmaceutically acceptable carrier) such as disintegrants, diluents, fillers, binders, buffering agents, lubricants, glidants, thickening agents, surfactants, flavors, colorants, preservatives and the like. Some excipients can serve multiple purposes.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose sodium (crosslinked sodium carboxymethylcellulose). The amount of disintegrant in the tablets according to the present invention may conveniently range from about 2.5 to about 15% w/w and preferably range from about 2.5 to 7% w/w, in particular range from about 2.5 to 5% w/w. Because disintegrants by their nature yield sustained release formulations when employed in bulk, it is advantageous to dilute them with an inert substance called a diluent or filler.

A variety of materials may be used as diluents or fillers. Examples are lactose monohydrate, anhydrous lactose, sucrose, dextrose, mannitol, sorbitol, starch, cellulose (e.g. micro-crystalline cellulose (Avicel™), silicifiedmicrocrystalline cellulose), dihydrated or anhydrous dibasic calcium phosphate, and others known in the art, and mixtures thereof (e.g. spray-dried mixture of lactose monohydrate (75%) with microcrystalline cellulose (25%) which is commercially available as Microcelac™) Preferred are microcrystalline cellulose and mannitol. The total amount of diluent or filler in the pharmaceutical compositions of the present invention may conveniently range from about 20% to about 95% w/w and preferably ranges from about 55% to about 95% w/w, or from about 70% to about 95% w/w, or from about 80% to about 95% w/w, or from about 85% to about 95%.

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, colloidal anhydrous silica talc, mixtures thereof, and others known in the art.

Interesting lubricants are magnesium stearate, and mixtures of magnesium stearate with colloidal silica, magnesium stearate being preferred. A preferred glidant is colloidal anhydrous silica.

If present, glidants generally comprise 0.2 to 7.0% w/w of the total composition weight, in particular 0.5 to 1.5% w/w, more in particular 1 to 1.5% w/w.

If present, lubricants generally comprise 0.2 to 7.0% w/w of the total composition weight, in particular 0.2 to 2% w/w, or 0.5 to 2% w/w, or 0.5 to 1.75% w/w, or 0.5 to 1.5% w/w.

Binders can optionally be employed in the pharmaceutical compositions of the present invention. Suitable binders are water-soluble polymers, such as alkylcelluloses such as methylcellulose; hydroxyalkylcelluloses such as hydroxymethylcellulose, hydroxyethylcellulose, hydroxypropylcellulose and hydroxybutylcellulose; hydroxyalkyl alkylcelluloses such as hydroxyethyl methylcellulose and hydroxypropyl methylcellulose; carboxyalkylcelluloses such as carboxymethylcellulose; alkali metal salts of carboxyalkylcelluloses such as sodium carboxymethylcellulose; carboxyalkylalkylcelluloses such as carboxymethylethylcellulose; carboxyalkylcellulose esters; starches; pectines such as sodium carboxymethylamylopectine; chitin derivates such as chitosan; di-, oligo- and polysaccharides such as trehalose, cyclodextrins and derivatives thereof, alginic acid, alkali metal and ammonium salts thereof, carrageenans, galactomannans, tragacanth, agar-agar, gummi arabicum, guar gummi and xanthan gummi; polyacrylic acids and the salts thereof; polymethacrylic acids, the salts and esters thereof, methacrylate copolymers; polyvinylpyrrolidone (PVP), polyvinylalcohol (PVA) and copolymers thereof, e.g. PVP-VA. Preferably, the water-soluble polymer is a hydroxyalkyl alkylcelluloses, such as for example hydroxypropylmethyl cellulose, e.g. hydroxypropylmethyl cellulose 15 cps.

Other excipients such as coloring agents and pigments may also be added to the compositions of the invention. Coloring agents and pigments include titanium dioxide and dyes suitable for food. A coloring agent or a pigment is an optional ingredient in the formulation of the invention, but when used the coloring agent can be present in an amount up to 3.5% w/w based on the total composition weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth, The amount of flavor may depend on a number of factors including the organoleptic effect desired. Generally the flavor will be present in an amount from about 0% to about 3% (w/w).

It is another object of the invention to provide a process of preparing a pharmaceutical composition as described herein, in particular in the form of a tablet or a capsule, characterized by blending a formaldehyde scavenger, in particular meglumine, and N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, with a pharmaceutically acceptable carrier and compressing said blend into tablets or filling said blend in capsules.

To prepare the pharmaceutical compositions of the invention, N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, as the active pharmaceutical ingredient, a formaldehyde scavenger, in particular meglumine, is combined in intimate admixture with a pharmaceutically acceptable carrier, which carrier may take a wide variety of forms as described herein.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof. Preferred forms are tablets and capsules.

In an aspect of the invention, N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered via the pharmaceutical compositions of the present invention in an amount sufficient to exert an anti-tumour activity.

In an aspect of the invention, the pharmaceutical compositions as described herein comprise N-(3,5-dimethoxyphenyl)-N'-(1-methylethyl)-N-[3-(1-methyl-1H-pyrazol-4-yl)quinoxalin-6-yl]ethane-1,2-diamine base.

In an aspect of the invention, the pharmaceutical compositions as described herein comprise a pharmaceutically acceptable salt of N-(3,5-dimethoxyphenyl)-N'-(1-methylethyl)-N-[3-(1-methyl-1H-pyrazol-4-yl)quinoxalin-6-yl]ethane-1,2-diamine, in particular N-(3,5-dimethoxyphenyl)-N'-(1-methylethyl)-N-[3-(1-methyl-1H-pyrazol-4-yl)quinoxalin-6-yl]ethane-1,2-diamine hydrochloride.

The invention also relates to a pharmaceutical package suitable for commercial sale comprising a container, a pharmaceutical composition as described herein, and associated with said package written matter.

The containers containing a pharmaceutical composition of the present invention, e.g. bottles, optionally contain a desiccant. In an aspect of the invention, the containers containing a pharmaceutical composition of the present invention, e.g. bottles, do not contain a desiccant. In an aspect of the invention the containers are HDPE bottles.

The containers containing a pharmaceutical composition of the present invention preferably comprise or consist of formaldehyde free material, such as for example formaldehyde free aluminium foil, e.g. in the case of blisters, e.g. PVC with aldehyde free aluminium foil blisters or Aclar® with aldehyde free aluminium foil blisters.

In an aspect of the invention, the container is a child resistant container, e.g. a bottle with a child resistant cap or a blister with a child resistant wallet.

The term "about" as used herein in connection with a numerical value is meant to have its usual meaning in the context of the numerical value. Where necessary the word "about" may be replaced by the numerical value 10%, or 5%, or 2%, or 1%. All documents cited herein are incorporated herein in their entirety.

Pharmaceutically Acceptable Salts or Solvates

The salt forms of N-(3,5-dimethoxyphenyl)-N'-(1-methylethyl)-N-[3-(1-methyl-1H-pyrazol-4-yl)quinoxalin-6-yl]ethane-1,2-diamine or of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, are typically pharmaceutically acceptable salts, and examples of pharmaceutically acceptable salts are discussed in Berge et al. (1977) "Pharmaceutically Acceptable Salts," *J. Pharm. Sci., Vol.* 66, pp. 1-19.

The salts of the present invention can be synthesized from the parent compound that contains a basic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the appropriate acid in water or in an organic solvent, or in a mixture of the two; generally, nonaqueous media such as ether, ethyl acetate, ethanol, isopropanol, or acetonitrile are used. The salts may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g.naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

N-(3,5-dimethoxyphenyl)-N'-(1-methylethyl)-N-[3-(1-methyl-1H-pyrazol-4-yl)quinoxalin-6-yl]ethane-1,2-diamine or salts thereof, and 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine or salts thereof, may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis.

A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed are any complexes (e.g. inclusion complexes or clathrates with compounds such as cyclodextrins, or complexes with metals) of the compounds.

Furthermore, N-(3,5-dimethoxyphenyl)-N'-(1-methylethyl)-N-[3-(1-methyl-1H-pyrazol-4-yl)quinoxalin-6-yl] ethane-1,2-diamine, a pharmaceutically acceptable salt thereof or a solvate thereof, or 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, a pharmaceutically acceptable salt thereof or a solvate thereof, may have one or more polymorph (crystalline) or amorphous forms and as such are intended to be included in the scope of the invention.

N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, or 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, a pharmaceutically acceptable salt thereof or a solvate thereof, include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. In one embodiment of the invention, the compounds contain no radioactive isotopes. Such compounds are preferred for therapeutic use. In another embodiment, however, the compound may contain one or more radioisotopes.

Compounds containing such radioisotopes may be useful in a diagnostic context.

Protein Tyrosine Kinases (PTK)

N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof inhibits or modulates the activity of certain tyrosine kinases, and thus the pharmaceutical compositions of the present invention will be useful in the treatment or prophylaxis, in particular the treatment, of disease states or conditions mediated by those tyrosine kinases, in particular FGFR (fibroblast growth factor receptor).

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1.

Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes. FGFR1 has also been linked to squamous lung cancer, colorectal cancer, glioblastoma, astrocytomas, prostate cancer, small cell lung cancer, melanoma, head and neck cancer, thyroid cancer, uterine cancer.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors. FGFR3 is also linked to endometrial and thyroid cancer.

Over expression of FGFR4 has been linked to poor prognosis in both prostate and thyroid carcinomas. In addition a germline polymorphism (Gy388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated. FGFR4 is also linked to astrocytomas, rhabdomyosarcoma.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the pharmaceutical compositions of the present invention will be useful in providing a means of preventing the growth or inducing apoptosis in tumours, particularly by inhibiting angiogenesis. It is therefore anticipated that the pharmaceutical compositions of the present invention will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with the pharmaceutical compositions of the present invention particularly beneficial, for instance patients with tumors, e.g. bladder or brain tumors, with FGFR3-TACC3 translocation.

Biological Activity and Therapeutic Uses

The pharmaceutical compositions of the present invention will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the pharmaceutical compositions of the present invention may be useful in alleviating or reducing the incidence of cancer.

N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof inhibits or modulates the activity of certain protein tyrosine kinases, in particular FGFR (fibroblast growth factor receptor). It is a selective, pan-FGFR inhibitor (inhibitor of FGFR1, 2, 3 and 4).

As a consequence of the activity in modulating or inhibiting FGFR by N-(3,5-dimethoxyphenyl)-N'-(1-methylethyl)-N-[3-(1-methyl-1H-pyrazol-4-yl)quinoxalin-6-yl] ethane-1,2-diamine, a pharmaceutically acceptable salt thereof or a solvate thereof, the pharmaceutical compositions of the present invention will be useful in providing a means of preventing the growth or inducing apoptosis of neoplasias, particularly by inhibiting angiogenesis. It is therefore anticipated that the pharmaceutical compositions of the present invention will prove useful in treating or preventing proliferative disorders such as cancers. In addition, the pharmaceutical compositions of the present invention could be useful in the treatment of diseases in which there is a disorder of proliferation, apoptosis or differentiation.

Particular tumours with activating mutants or upregulation or overexpression of any of the isoforms of FGFR such as FGFR1, FGFR2 or FGFR3 or FGFR4 may be particularly sensitive to the pharmaceutical compositions of the present invention and thus patients as discussed herein with such particular tumours may also find treatment with the pharmaceutical compositions of the present invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

Non-small cell lung cancer (NSCLC) encompasses advanced and refractory NSCLC.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The pharmaceutical compositions of the present invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the pharmaceutical compositions of the present invention can be used to treat gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

A further subset of cancers includes hepatocellular cancer harboring FGF19 amplification or overexpression. An aspect of the invention is a method of treating hepatocellular cancer in a patient harboring FGF19 amplification or overexpression comprising administering to said patient a pharmaceutical composition according to the invention.

A subset of cancer includes cholangiocarcinoma, in particular cholangiocarcinoma with FGFR genomic alterations (translocations, fusions and/or mutations).

A subset of cancer includes advanced or refractory NSCLC, breast cancer, glioblastoma multiforme, urothelial cancer, ovarian cancer, head and neck cancer, oesophageal cancer, gastric cancer and cholangiocarcinoma, in particular advanced or refractory NSCLC, breast cancer, glioblastoma multiforme, urothelial cancer, ovarian cancer, head and neck cancer, oesophageal cancer, gastric cancer and cholangiocarcinoma with FGFR genomic alterations (translocations, fusions and/or mutations).

A subset of cancer includes metastatic or surgically unresectable urothelial cancer, in particular metastatic or surgically unresectable urothelial cancer with FGFR genomic alterations (translocations, fusions and/or mutations).

A subset of cancer includes urothelial cancer, in particular urothelial cancer with FGFR genomic alterations (translocations, fusions and/or mutations).

A subset of cancer includes non-muscle-invasive bladder cancer, in particular non-muscle-invasive bladder cancer with FGFR genomic alterations (translocations, fusions and/or mutations).

A subset of cancer includes non small cell lung cancer (NSCLC), squamous lung cancer and non-squamous lung cancer, in particular non small cell lung cancer (NSCLC), squamous lung cancer and non-squamous lung cancer with FGFR genomic alterations (translocations, fusions and/or mutations).

A subset of cancer includes sarcoma, e.g. rhabdomyosarcoma, in particular sarcoma, e.g. rhabdomyosarcoma, with FGFR genomic alterations (translocations, fusions and/or mutations).

The pharmaceutical compositions of the present invention may be particularly useful in the treatment or prevention of breast cancer in particular Classic Lobular Carcinomas (CLC).

As the compound in the pharmaceutical compositions of the present invention has FGFR4 activity the pharmaceutical compositions of the present invention will also be useful in the treatment of prostate or pituitary cancers, or they will be useful in the treatment of breast cancer, lung cancer, prostate cancer, liver cancer (HCC; hepatocellular cancer) or lung cancer.

In particular the pharmaceutical compositions of the present invention, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the pharmaceutical compositions of the present invention are useful in the treatment of multiple myeloma (in particular multiple myeloma with t(4;14) translocation or overexpressing FGFR3), prostate cancer (hormone refractory prostate carcinomas), endometrial cancer (in particular endometrial tumours with activating mutations in FGFR2) and breast cancer (in particular lobular breast cancer).

In particular the pharmaceutical compositions of the present invention are useful in the treatment of lobular carcinomas such as CLC (Classic lobular carcinoma).

As the compound in the pharmaceutical compositions of the present invention has activity against FGFR3 the pharmaceutical compositions of the present invention will be useful in the treatment of multiple myeloma and bladder cancer.

In particular, the pharmaceutical compositions of the present invention have activity against tumours with FGFR3-TACC3 translocation, in particular bladder or brain or urothelial tumours with FGFR3-TACC3 translocation.

In particular the pharmaceutical compositions of the present invention are useful for the treatment of t(4;14) translocation positive multiple myeloma.

In one embodiment the pharmaceutical compositions of the present invention may be useful for the treatment of sarcoma. In one embodiment the pharmaceutical compositions of the present invention may be useful for the treatment of lung cancer, e.g. squamous cell carcinoma.

As the compound in the pharmaceutical compositions of the present invention has activity against FGFR2 the pharmaceutical compositions of the present invention will be useful in the treatment of endometrial, ovarian, gastric, hepatocellular, uterine, cervix and colorectal cancers. FGFR2 is also overexpressed in epithelial ovarian cancer, therefore the compositions of the invention may be specifically useful in treating ovarian cancer such as epithelial ovarian cancer.

In one embodiment, the pharmaceutical compositions of the present invention may be useful for the treatment of lung cancer, in particular NSCLC, squamous cell carcinoma, liver cancer, kidney cancer, breast cancer, colon cancer, colorectal cancer, prostate cancer.

In one embodiment, the pharmaceutical compositions of the present invention may be useful for the treatment of metastatic or surgically unresectable urothelial cancer, in particular metastatic or surgically unresectable urothelial cancer with FGFR genomic alterations (translocations, fusions and/or mutations).

In one embodiment, the pharmaceutical compositions of the present invention may be useful for the treatment of urothelial cancer, in particular urothelial cancer with FGFR genomic alterations (translocations, fusions and/or mutations).

In one embodiment, the pharmaceutical compositions of the present invention may be useful for the treatment of non-muscle-invasive bladder cancer, in particular non-muscle-invasive bladder cancer with FGFR genomic alterations (translocations, fusions and/or mutations).

In one embodiment, the pharmaceutical compositions of the present invention may be useful for the treatment of non small cell lung cancer (NSCLC), squamous lung cancer and non-squamous lung cancer, in particular non small cell lung cancer (NSCLC), squamous lung cancer and non-squamous lung cancer with FGFR genomic alterations (translocations, fusions and/or mutations).

In one embodiment, the pharmaceutical compositions of the present invention may be useful for the treatment of sarcoma, e.g. rhabdomyosarcoma, in particular sarcoma, e.g. rhabdomyosarcoma, with FGFR genomic alterations (translocations, fusions and/or mutations).

In one embodiment, the pharmaceutical compositions of the present invention may be useful for the treatment of advanced or refractory NSCLC, breast cancer, glioblastoma multiforme, urothelial cancer, ovarian cancer, head and neck cancer, oesophageal cancer, gastric cancer and cholangiocarcinoma, in particular advanced or refractory NSCLC, breast cancer, glioblastoma multiforme, urothelial cancer, ovarian cancer, head and neck cancer, oesophageal cancer, gastric cancer and cholangiocarcinoma with FGFR genomic alterations (translocations, fusions and/or mutations).

In one embodiment, the pharmaceutical compositions of the present invention may be useful for the treatment of cholangiocarcinoma, in particular cholangiocarcinoma with FGFR genomic alterations (translocations, fusions and/or mutations).

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR signalling may be determined by means of a cell growth assay as set out below or by a method as set out in the section headed "Methods of Diagnosis".

The pharmaceutical compositions of the present invention may be particularly useful in the treatment or prevention of cancers of a type associated with or characterised by the presence of elevated levels of FGFR.

The pharmaceutical compositions of the present invention may be useful for the treatment of the adult population. The pharmaceutical compositions of the present invention may be useful for the treatment of the pediatric population. The pharmaceutical compositions of the present invention may be useful for the treatment of the geriatric population.

In an aspect of the invention, the pharmaceutical compositions are administered on a continuous daily basis, preferably once daily. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In an aspect, the daily dose administered on a continuous daily basis, is 6 mg or 8 mg base.

Thus an aspect of the present invention is a method for the prophylaxis of cancer in a subject, in particular a human, or a method for treating cancer in a patient, in particular a human, comprising administering to the subject or the patient a pharmaceutical composition as described herein daily, preferably every day once daily. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In an aspect, the daily dose administered on a continuous daily basis, is 6 mg or 8 mg base.

An aspect of the present invention is the use of a pharmaceutical composition as described herein for the manufacture of a medicament for the prophylaxis or the treatment of cancer, in particular for the treatment of cancer, wherein the medicament is administered or is to be administered daily. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In an aspect, the daily dose administered on a continuous daily basis, is 6 mg or 8 mg base.

An aspect of the present invention is a pharmaceutical composition as described herein for use in the prophylaxis or the treatment of cancer, in particular in the treatment of cancer, wherein the composition is administered or is to be administered daily. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In an aspect, the daily dose administered on a continuous daily basis, is 6 mg or 8 mg base.

In an aspect of the present invention, the pharmaceutical compositions are administered on an intermittent dosing schedule, preferably a number of consecutive days with daily administration of the pharmaceutical compositions of the present invention followed by a number of days wherein no such composition is administered (drug-free period). Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base.

An intermittent dosing schedule of the present invention is administration of the pharmaceutical compositions of the present invention daily for 3 weeks (3 weeks on; 21 consecutive days of drug administration) followed by 1 week wherein no such composition is administered (1 week off, 7 consecutive days of drug free period). This cycle is then repeated. The daily dose is preferably administered once daily.

Thus an aspect of the present invention is a method for the prophylaxis of cancer in a subject, in particular a human, or a method for treating cancer in a patient, in particular a human, comprising administering to the subject or the patient a pharmaceutical composition as described herein on an intermittent dosing schedule.

An aspect of the invention is a method for the prophylaxis of cancer in a subject, in particular a human, or a method of treating cancer in a cancer patient, in particular a human, comprising administering to the subject or the patient a composition of the present invention daily for 3 weeks (3 weeks on), followed by 1 week off and repeating this cycle of 3 weeks on, 1 week off. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In particular, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof is 6 mg base equivalent, more in particular 6 mg base equivalent once a day for 3 weeks, followed by 1 week off (no administration of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof).

An intermittent dosing schedule of the present invention is administration of the pharmaceutical compositions of the present invention for 1 week (1 week on; 7 consecutive days of drug administration) followed by 1 week wherein no such composition is administered (1 week off, 7 consecutive days of drug free period). This cycle is then repeated.

An aspect of the invention is a method for the prophylaxis of cancer in a subject or a method of treating cancer in a cancer patient comprising administering to the subject or the patient a composition of the present invention daily for 1 week (1 week on), followed by 1 week off and repeating this cycle of 1 week on, 1 week off. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In particular, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof is 10 mg or 12 mg base equivalent, more in particular 10 mg base equivalent once a day for 1 week, followed by 1 week off (no administration of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof).

An aspect of the present invention is the use of a pharmaceutical composition as described herein for the manufacture of a medicament for the prophylaxis or the treatment of cancer, in particular for the treatment of cancer, wherein the medicament is administered or is to be administered daily for 3 weeks (3 weeks on), followed by 1 week off (no administration of the medicament) and wherein said cycle of 3 weeks on, 1 week off is repeated. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In particular, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof is 6 mg base equivalent, more in particular 6 mg base equivalent once a day for 3 weeks, followed by 1 week off (no administration of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof).

An aspect of the present invention is a pharmaceutical composition as described herein for use in the prophylaxis or the treatment of cancer, in particular in the treatment of cancer, wherein the composition is administered or is to be administered daily for 3 weeks (3 weeks on), followed by 1 week off (no administration of the medicament) and wherein said cycle of 3 weeks on, 1 week off is repeated. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In particular, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof is 6 mg base equivalent, more in particular 6 mg base equivalent once a day for 3 weeks, followed by 1 week off (no administration of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof).

An aspect of the present invention is the use of a pharmaceutical composition as described herein for the manufacture of a medicament for the prophylaxis or the treatment of cancer, in particular for the treatment of cancer, wherein the medicament is administered or is to be administered daily for 1 week (1 week on), followed by 1 week off (no administration of the medicament) and wherein said cycle of 1 week on, 1 week off is repeated. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In particular, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof is 10 mg or 12 mg base equivalent, more in particular 10 mg base equivalent once a day for 1 week, followed by 1 week off (no administration of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof).

An aspect of the present invention is a pharmaceutical composition as described herein for use in the prophylaxis or the treatment of cancer, in particular in the treatment of cancer, wherein the composition is administered or is to be administered daily for 1 week (1 week on), followed by 1 week off (no administration of the medicament) and wherein said cycle of 1 week on, 1 week off is repeated. Preferably, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof ranges from 6 to 12 mg base equivalent, or is 6 mg base equivalent, 7 mg base equivalent, 8 mg base equivalent, 9 mg base equivalent, 10 mg base equivalent, 11 mg base equivalent or 12 mg base equivalent. The daily dose is preferably administered once daily. Preferably the composition comprises N-(3,5-dimethoxyphenyl)-N'-(1-methylethyl)-N-[3-(1-methyl-1H-pyrazol-4-yl)quinoxalin-6-yl]ethane-1,2-diamine base. In particular, the daily dose of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof is 10 mg or 12 mg base equivalent, more in particular 10 mg base equivalent once a day for 1 week, followed by 1 week off (no administration of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof).

The daily dose of N-(3,5-dimethoxyphenyl)-N'-(1-methylethyl)-N-[3-(1-methyl-H-pyrazol-4-yl)quinoxalin-6-yl]ethane-1,2-diamine, a pharmaceutically acceptable salt thereof or a solvate thereof can be administered via one pharmaceutical composition according to the present invention, or via more than one pharmaceutical compositions according to the present invention. These more than one pharmaceutical compositions according to the present invention may be administered separately, simultaneously or sequentially.

An aspect of the present invention is the prophylaxis or the treatment, in particular the treatment, of metastatic or surgically unresectable urothelial cancer, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of metastatic or surgically unresectable urothelial cancer, in particular with FGFR genomic alterations (translocations, fusions and/or mutations), wherein 8 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of urothelial cancer, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of urothelial cancer, in particular with FGFR genomic alterations (translocations, fusions and/or mutations), wherein 8 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of non small cell lung cancer (NSCLC), squamous lung cancer and non-squamous lung cancer, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of non small cell lung cancer (NSCLC), squamous lung cancer and non-squamous lung cancer, in particular with FGFR genomic alterations (translocations, fusions and/or mutations), wherein 8 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of advanced or refractory NSCLC, breast cancer, glioblastoma multiforme, urothelial cancer, ovarian cancer, head and neck cancer, oesophageal cancer, gastric cancer and cholangiocarcinoma, in particular with FGFR genomic alterations (translocations, fusions and/or mutations), wherein 9 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of advanced or refractory NSCLC, breast cancer, glioblastoma multiforme, urothelial cancer, ovarian cancer, head and neck cancer, oesophageal cancer, gastric cancer and cholangiocarcinoma, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of advanced or refractory NSCLC, breast cancer, glioblastoma multiforme, urothelial cancer, ovarian cancer, head and neck cancer, oesophageal cancer, gastric cancer and cholangiocarcinoma, in particular with FGFR genomic alterations (translocations, fusions and/or mutations), wherein 8 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of cholangiocarcinoma, in particular with FGFR genomic alterations (translocations, fusions and/or mutations), wherein 9 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of cholangiocarcinoma, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of cholangiocarcinoma, in particular with FGFR genomic alterations (translocations, fusions and/or mutations), wherein 8 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein.

An aspect of the present invention is the prophylaxis or the treatment, in particular the treatment, of metastatic or surgically unresectable urothelial cancer, in particular with FGFR genomic alterations (translocations, fusions and/or mutations), wherein 10 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on), followed by 1 week off (no administration of the medicament) and wherein said cycle of 1 week on, 1 week off is repeated.

An aspect of the present invention is the prophylaxis or the treatment, in particular the treatment, of metastatic or surgically unresectable urothelial cancer, in particular with FGFR genomic alterations (translocations, fusions and/or mutations), wherein 12 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on), followed by 1 week off (no administration of the medicament) and wherein said cycle of 1 week on, 1 week off is repeated.

An aspect of the present invention is the prophylaxis or the treatment, in particular the treatment, of metastatic or surgically unresectable urothelial cancer, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 3 weeks (3 weeks on), followed by 1 week off (no administration of the medicament) and wherein said cycle of 3 weeks on, 1 week off is repeated.

An aspect of the present invention is the prophylaxis or the treatment, in particular the treatment, of urothelial cancer, in particular with FGFR genomic alterations (translocations, fusions and/or mutations), wherein 10 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on), followed by 1 week off (no administration of the medicament) and wherein said cycle of 1 week on, 1 week off is repeated.

An aspect of the present invention is the prophylaxis or the treatment, in particular the treatment, of urothelial cancer, in particular with FGFR genomic alterations (translocations, fusions and/or mutations), wherein 12 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on), followed by 1 week off (no administration of the medicament) and wherein said cycle of 1 week on, 1 week off is repeated.

An aspect of the present invention is the prophylaxis or the treatment, in particular the treatment, of urothelial cancer, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 3 weeks (3 weeks on), followed by 1 week off (no administration of the medicament) and wherein said cycle of 3 weeks on, 1 week off is repeated.

An aspect of the present invention is the prophylaxis or the treatment, in particular the treatment, of non small cell lung cancer (NSCLC), squamous lung cancer and non-squamous lung cancer, in particular with FGFR genomic alterations (translocations, fusions and/or mutations), wherein 10 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on), followed by 1 week off (no administration of the medicament) and wherein said cycle of 1 week on, 1 week off is repeated.

An aspect of the present invention is the prophylaxis or the treatment, in particular the treatment, of non small cell lung cancer (NSCLC), squamous lung cancer and non-squamous lung cancer, in particular with FGFR genomic alterations (translocations, fusions and/or mutations), wherein 12 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on), followed by 1 week off (no administration of the medicament) and wherein said cycle of 1 week on, 1 week off is repeated.

An aspect of the present invention is the prophylaxis or the treatment, in particular the treatment, of non small cell lung cancer (NSCLC), squamous lung cancer and non-squamous lung cancer, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 3 weeks (3 weeks on), followed by 1 week off (no administration of the medicament) and wherein said cycle of 3 weeks on, 1 week off is repeated.

An aspect of the present invention is the prophylaxis or the treatment, in particular the treatment, of advanced or refractory NSCLC, breast cancer, glioblastoma multiforme, urothelial cancer, ovarian cancer, head and neck cancer, oesophageal cancer, gastric cancer and cholangiocarcinoma, in particular with FGFR genomic alterations (translocations, fusions and/or mutations), wherein 10 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on) followed by 1 week off (no administration of the medicament) and wherein said cycle of 1 week on, 1 week off is repeated.

An aspect of the present invention is the prophylaxis or the treatment, in particular the treatment, of advanced or refractory NSCLC, breast cancer, glioblastoma multiforme, urothelial cancer, ovarian cancer, head and neck cancer, oesophageal cancer, gastric cancer and cholangiocarcinoma, in particular with FGFR genomic alterations (translocations, fusions and/or mutations), wherein 12 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on) followed by 1 week off (no administration of the medicament) and wherein said cycle of 1 week on, 1 week off is repeated.

An aspect of the present invention is the prophylaxis or the treatment, in particular the treatment, of advanced or refractory NSCLC, breast cancer, glioblastoma multiforme, urothelial cancer, ovarian cancer, head and neck cancer, oesophageal cancer, gastric cancer and cholangiocarcinoma, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 3 weeks (3 weeks on) followed by 1 week off (no administration of the medicament) and wherein said cycle of 3 weeks on, 1 week off is repeated.

An aspect of the present invention is the prophylaxis or the treatment, in particular the treatment, of cholangiocarcinoma, in particular with FGFR genomic alterations (translocations, fusions and/or mutations), wherein 10 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on) followed by 1 week off (no administration of the medicament) and wherein said cycle of 1 week on, 1 week off is repeated.

An aspect of the present invention is the prophylaxis or the treatment, in particular the treatment, of cholangiocarcinoma, in particular with FGFR genomic alterations (translocations, fusions and/or mutations), wherein 12 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 1 week (1 week on) followed by 1 week off (no administration of the medicament) and wherein said cycle of 1 week on, 1 week off is repeated.

An aspect of the present invention is the prophylaxis or the treatment, in particular the treatment, of cholangiocarcinoma, in particular with FGFR genomic alterations (translocations, fusions and/or mutations), wherein 6 mg of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof, in particular N-(3,5-dimethoxyphenyl)-N'-(1-methylethyl)-N-[3-(1-methyl-1H-pyrazol-4-yl)quinoxalin-6-yl]ethane-1,2-diamine base, is administered or is to be administered daily, in particular once daily, as one or more, in particular more than one, pharmaceutical compositions as described herein for 3 weeks (3 weeks on) followed by 1 week off (no administration of the medicament) and wherein said cycle of 3 weeks on, 1 week off is repeated.

The pharmaceutical compositions of the present invention may be used in combination with other anticancer agents. For example, it may be beneficial to combine the pharmaceutical compositions of the present invention with another agent which acts via a different mechanism to regulate cell growth thus treating different characteristic features of cancer development. Examples of such combinations are set out below.

The pharmaceutical compositions of the present invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions wherein the pharmaceutical compositions of the present invention may be useful consists of inflammatory diseases, cardiovascular diseases and wound healing.

FGFR is also known to play a role in apoptosis, angiogenesis, proliferation, differentiation and transcription and therefore the pharmaceutical compositions of the present invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the pharmaceutical compositions of the present invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The pharmaceutical compositions of the present invention may be particularly useful in the treatment or prevention of skeletal diseases. Particular skeletal diseases are achondroplasia or thanatophoric dwarfism (also known as thanatophoric dysplasia).

The pharmaceutical compositions of the present invention, may be particularly useful in the treatment or prevention in pathologies in which progressive fibrosis is a symptom. Fibrotic conditions in which the pharmaceutical compositions of the present invention may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the pharmaceutical compositions of the present invention may also be useful in the treatment of lung fibrosis in particular in idiopathic pulmonary fibrosis.

The over-expression and activation of FGFR in tumor-associated vasculature has also suggested a role for the pharmaceutical compositions of the present invention in preventing and disrupting initiation of tumor angiogenesis. In particular, the pharmaceutical compositions of the present invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The invention provides pharmaceutical compositions which may be useful in preventing or treating, in particular in treating, disease states or conditions mediated by FGFR kinases.

In one embodiment, there is provided a pharmaceutical composition for use in the prophylaxis or treatment, in particular in the treatment, of a disease state or condition mediated by a FGFR kinase.

Thus, for example, the pharmaceutical compositions of the present invention may be useful in alleviating or reducing the incidence of cancer. Therefore, in a further embodiment, there is provided a pharmaceutical composition as described herein for use in the prophylaxis or treatment, in particular the treatment, of cancer. In one embodiment, the pharmaceutical composition as defined herein is for use in the prophylaxis or treatment of FGFR-dependent cancer. In one embodiment, the pharmaceutical composition as defined herein is for use in the prophylaxis or treatment of cancer mediated by FGFR kinases.

Accordingly, the invention provides inter alia:
A method for the prophylaxis or treatment of a disease state or condition mediated by a FGFR kinase, which method comprises administering to a subject in need thereof a pharmaceutical composition as defined herein.
A method for the prophylaxis or treatment of a disease state or condition as described herein, which method comprises administering to a subject in need thereof a pharmaceutical composition as defined herein.
A method for the prophylaxis or treatment of cancer, which method comprises administering to a subject in need thereof a pharmaceutical composition as defined herein.
A method for alleviating or reducing the incidence of a disease state or condition mediated by a FGFR kinase, which method comprises administering to a subject in need thereof a pharmaceutical composition as defined herein.

A method of inhibiting a FGFR kinase, which method comprises contacting the kinase with a kinase-inhibiting pharmaceutical composition as defined herein.

A method of modulating a cellular process (for example cell division) by inhibiting the activity of a FGFR kinase using a pharmaceutical composition as defined herein.

A pharmaceutical composition as defined herein for use to modulate a cellular process (for example cell division) by inhibiting the activity of a FGFR kinase.

A pharmaceutical composition as defined herein for use in the prophylaxis or treatment of cancer, in particular the treatment of cancer.

A pharmaceutical composition as defined herein for use to modulate (e.g. inhibit) FGFR.

The use of a pharmaceutical composition as defined herein for the manufacture of a medicament for the prophylaxis or treatment of a disease state or condition mediated by a FGFR kinase, the pharmaceutical composition as defined herein.

The use of a pharmaceutical composition as defined herein for the manufacture of a medicament for the prophylaxis or treatment of a disease state or condition as described herein.

The use of a pharmaceutical composition as defined herein for the manufacture of a medicament for the prophylaxis or treatment, in particular the treatment, of cancer.

The use of a pharmaceutical composition as defined herein for the manufacture of a medicament for modulating (e.g. inhibiting) the activity of FGFR.

Use of a pharmaceutical composition as defined herein in the manufacture of a medicament for modulating a cellular process (for example cell division) by inhibiting the activity of a FGFR kinase.

The use of a pharmaceutical composition as defined herein for the manufacture of a medicament for prophylaxis or treatment of a disease or condition characterised by up-regulation of a FGFR kinase (e.g. FGFR1 or FGFR2 or FGFR3 or FGFR4).

The use of a pharmaceutical composition as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a pharmaceutical composition as defined herein for the manufacture of a medicament for the prophylaxis or treatment of cancer in a patient selected from a sub-population possessing a genetic aberration of FGFR3 kinase.

The use of a pharmaceutical composition as defined herein for the manufacture of a medicament for the prophylaxis or treatment of cancer in a patient who has been diagnosed as forming part of a sub-population possessing a genetic aberration of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a pharmaceutical composition as defined herein.

A method for alleviating or reducing the incidence of a disease or condition characterised by up-regulation of a FGFR kinase (e.g. FGFR1 or FGFR2 or FGFR3 or FGFR4), the method comprising administering a pharmaceutical composition as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberration of FGFR3 gene; and (ii) where the patient does possess the said variant, thereafter administering to the patient a pharmaceutical composition as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a pharmaceutical composition as defined herein having FGFR kinase inhibiting activity.

A method for the prophylaxis or treatment of (or alleviating or reducing the incidence of) a disease state or condition characterised by a FGFR mutation, translocation, fusion, in particular a FGFR2 or FGFR3 mutation, translocation, fusion; which method comprises (i) subjecting a patient to a diagnostic test to detect a marker characteristic of a FGFR mutation, translocation, fusion, in particular a FGFR2 or FGFR3 mutation, translocation, fusion, and (ii) where the diagnostic test is indicative of a FGFR mutation, translocation, fusion, in particular a FGFR2 or FGFR3 mutation, translocation, fusion, thereafter administering to the patient a pharmaceutical composition as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The pharmaceutical compositions of the present invention would therefore find particular application in relation to cancers which express a mutated molecular target such as FGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Methods of Diagnosis

Prior to administration of a pharmaceutical composition of the present invention, a patient may be screened to determine whether a disease or condition from which the patient is or may be suffering is one which would be susceptible to treatment with a compound having activity against FGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR or to sensitisation of a pathway to normal FGFR activity, or to upregulation of these growth factor signalling pathways such as growth factor ligand levels or growth factor ligand activity or to upregulation of a biochemical pathway downstream of FGFR activation.

Examples of such abnormalities that result in activation or sensitisation of the FGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T674I of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR. The term diagnosis includes screening. By marker we include genetic markers including, for example, the measurement of DNA composition to identify mutations of FGFR. The term marker also includes markers which are characteristic of up regulation of FGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR may mean that the patient would be particularly suitable for treatment with a FGFR inhibitor and hence with a pharmaceutical composition as defined herein. Tumours may preferentially be screened for presence of a FGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3$^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA Using a (dT) 24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, or detection of FGFR variants or mutants could be applicable in the present case.

Abnormal levels of proteins such as FGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR including the isoforms thereof, include the measurement of microvessel density. This can for example be measured using methods described by Orre and Rogers (Int J Cancer (1999), 84(2) 101-8). Assay methods also include the use of markers.

Therefore all of these techniques could also be used to identify tumours particularly suitable for treatment with the pharmaceutical compositions of the present invention.

The pharmaceutical compositions of the present invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer. The pharmaceutical compositions of the present invention are particular useful in treatment of a patient having a FGFR3-TACC3 translocation.

Therefore in a further aspect the invention includes use of a pharmaceutical composition of the present invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a pharmaceutical composition of the present invention for use in the prophylaxis or treatment of cancer in a patient selected from a sub-population possessing a variant of the FGFR gene (for example G697C mutation in FGFR3 and Gly388Arg polymorphism in FGFR4).

In an aspect of the invention, the pharmaceutical compositions as described herein are useful for the treatment of cancer, in particular bladder cancer, urothelial cancer, metastatic urothelial cancer, surgically unresectable urothelial cancer, breast cancer, glioblastoma, lung cancer, non small cell lung cancer, squamous lung cancer, pulmonary adenocarcinoma.

In an aspect of the invention, the pharmaceutical compositions as described herein are useful for the treatment of cancer, in particular gastric cancer, cholangiocarcinoma, esophageal cancer, hepatocellular cancer, non-squamous lung cancer, in particular with FGFR genomic alterations (translocations, fusions and/or mutations).

As another aspect of the present invention, a combination of a pharmaceutical composition of the present invention with another anticancer agent is envisaged, especially for use as a medicine, more specifically for use in the treatment of cancer or related diseases as described herein.

For the treatment of the above conditions, the pharmaceutical compositions of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoiden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors, cmet inhibitors) for example flavoperidol, imatinib mesylate, erlotinib, gefitinib, dasatinib, lapatinib, lapatinib ditosylate, sorafenib, sunitinib, sunitinib maleate, temsirolimus, 6-{difluoro[6-(1-methyl-1H-pyrazol-4-yl)[1,2,4]triazolo[4,3-b]pyridazin-3-yl]methyl}quinoline or a pharmaceutically ac ceptable salt thereof, 6-[difluoro(6-pyridin-4-yl[1,2,4]triazolo[4,3-b]pyridazin-3-yl)methyl]quinoline or a pharmaceutically acceptable salt thereof;

farnesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN.41 or bortezomib;

Yondelis-trabectedin;

agents impacting on the immune-system pertaining to anticancer activity such as, but not limited to, anti-CTLA4, anti-PD-1, anti-PDL-1, OX40, anti-cancer vaccines;

radiation therapy in the form of external beam radiation or radio-isotopes as implantable sources or temporarily applied source or radio-isotopes conjugated to other molecules;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

a steroidal cytochrome P450 17alpha-hydroxylase-17,20-lyase inhibitor (CYP17), e.g. abiraterone, abiraterone acetate.

an antibody that blocks the interaction between PD-1 (programmed cell death 1) and PD-L1 (programmed death-ligand 1).

In one embodiment, the present invention relates to a combination of a pharmaceutical composition according to the present invention, and 6-{difluoro[6-(1-methyl-1H-pyrazol-4-yl)[1,2,4]triazolo[4,3-b]pyridazin-3-yl]methyl}quinoline or a pharmaceutically acceptable salt thereof.

In one embodiment, the present invention relates to a combination of a pharmaceutical composition according to the present invention, and 6-[difluoro(6-pyridin-4-yl[1,2,4]triazolo[4,3-b]pyridazin-3-yl)methyl]quinoline or a pharmaceutically acceptable salt thereof.

In one embodiment, the present invention relates to a pharmaceutical composition as described herein further comprising 6-{difluoro[6-(1-methyl-1H-pyrazol-4-yl)[1,2,4]triazolo[4,3-b]pyridazin-3-yl]methyl}quinoline or a pharmaceutically acceptable salt thereof.

In one embodiment, the present invention relates to a pharmaceutical composition as described herein further comprising 6-[difluoro(6-pyridin-4-yl[1,2,4]triazolo[4,3-b]pyridazin-3-yl)methyl]quinoline or a pharmaceutically acceptable salt thereof.

The pharmaceutical compositions of the present invention also have therapeutic applications in sensitising tumour cells for radiotherapy and chemotherapy.

Hence the pharmaceutical compositions of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition as described herein and further comprising the one or more other medicinal agent together with a pharmaceutical carrier.

The present invention further relates to the use of a combination according to the invention in the manufacture of a pharmaceutical composition for inhibiting the growth of tumour cells.

The present invention further relates to a product containing a pharmaceutical composition as described herein and as further active ingredient one or more anticancer agent, as a combined preparation for simultaneous, separate or sequential use in the treatment of patients suffering from cancer.

The one or more other medicinal agents and the pharmaceutical composition according to the present invention may be administered simultaneously (e.g. in separate or unitary compositions) or sequentially in either order. In the latter case, the two or more components will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and composition of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound contained in the pharmaceutical compositions according to the present invention and the one or more other anticancer agent(s) when given as a combination may be determined by the person skilled in the art. Said ratio and the exact dosage and frequency of administration depends on the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art.

Furthermore, it is evident that the effective daily amount may be lowered or increased depending on the response of the treated subject and/or depending on the evaluation of the physician prescribing the compositions of the instant invention. A particular weight ratio for N-(3,5-dimethoxyphenyl)-N'-(1-methylethyl)-N-[3-(1-methyl-H-pyrazol-4-yl)quinoxalin-6-yl]ethane-1,2-diamine, a pharmaceutically acceptable salt thereof or a solvate thereof and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m²) of body surface area, for example 50 to 400 mg/m², particularly for cisplatin in a dosage of about 75 mg/m² and for carboplatin in about 300 mg/m² per course of treatment.

The taxane compound is advantageously administered in a dosage of 50 to 400 mg per square meter (mg/m²) of body surface area, for example 75 to 250 mg/m², particularly for paclitaxel in a dosage of about 175 to 250 mg/m² and for docetaxel in about 75 to 150 mg/m² per course of treatment.

The camptothecin compound is advantageously administered in a dosage of 0.1 to 400 mg per square meter (mg/m²) of body surface area, for example 1 to 300 mg/m², particularly for irinotecan in a dosage of about 100 to 350 mg/m² and for topotecan in about 1 to 2 mg/m² per course of treatment.

The anti-tumour podophyllotoxin derivative is advantageously administered in a dosage of 30 to 300 mg per square meter (mg/m²) of body surface area, for example 50 to 250 mg/m², particularly for etoposide in a dosage of about 35 to 100 mg/m² and for teniposide in about 50 to 250 mg/m² per course of treatment.

The anti-tumour vinca alkaloid is advantageously administered in a dosage of 2 to 30 mg per square meter (mg/m²) of body surface area, particularly for vinblastine in a dosage of about 3 to 12 mg/m², for vincristine in a dosage of about 1 to 2 mg/m², and for vinorelbine in dosage of about 10 to 30 mg/m² per course of treatment.

The anti-tumour nucleoside derivative is advantageously administered in a dosage of 200 to 2500 mg per square meter (mg/m²) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

These dosages may be administered for example once, twice or more per course of treatment, which may be repeated for example every 7, 14, 21 or 28 days.

EXAMPLES

Example 1

| Composition tablet 1 | |
|---|---|
| N-(3,5-dimethoxyphenyl)-N'-(1-methylethyl)-N-[3-(1-methyl-1H-pyrazol-4-yl)quinoxalin-6-yl]ethane-1,2-diamine | 3 mg |
| Meglumine | 1.5 mg |
| Mannitol | from 20% to 95% w/w |
| Microcrystalline cellulose | from 20% to 95% w/w |
| Croscarmellose sodium | from 2.5 to 5% w/w |
| Magnesium stearate | from 0.5 to 1.5% w/w |
| Total weight of the tablet: 150 mg. | |
| Composition tablet 2 | |
| N-(3,5-dimethoxyphenyl)-N'-(1-methylethyl)-N-[3-(1-methyl-1H-pyrazol-4-yl)quinoxalin-6-yl]ethane-1,2-diamine | 4 mg |
| Meglumine | 2 mg |
| Mannitol | from 20% to 95% w/w |
| Microcrystalline cellulose | from 20% to 95% w/w |
| Croscarmellose sodium | from 2.5 to 5% w/w |
| Magnesium stearate | from 0.5 to 1.5% w/w |
| Total weight of the tablet: 200 mg. | |
| Composition tablet 3 | |
| N-(3,5-dimethoxyphenyl)-N'-(1-methylethyl)-N-[3-(1-methyl-1H-pyrazol-4-yl)quinoxalin-6-yl]ethane-1,2-diamine | 5 mg |
| Meglumine | 2.5 mg |
| Mannitol | from 20% to 95% w/w |
| Microcrystalline cellulose | from 20% to 95% w/w |
| Croscarmellose sodium | from 2.5 to 5% w/w |
| Magnesium stearate | from 0.5 to 1.5% w/w |
| Total weight of the tablet: 250 mg. | |

Preparation of the Tablets

Appropriate amounts of N-(3,5-dimethoxyphenyl)-N'-(1-methylethyl)-N-[3-(1-methyl-1H-pyrazol-4-yl)quinoxalin-6-yl]ethane-1,2-diamine, mannitol, meglumine and croscarmellose sodium were co-sieved. An appropriate amount of microcrystalline cellulose was sieved. Both fractions were blended, milled and blended again. An appropriate amount of magnesium stearate was sieved and added to the blend. Said blend was compressed into tablets. The resulting tablets were film-coated with Opadry© II 85F92209.

Consumption of Meglumine as a Function of Time

To evaluate the stabilizing effect of meglumine in tablets of the present invention, the consumption of meglumine in the tablets as a function of time was determined.

Film-coated tablets according to the present invention were stored in bottles without desiccant under different conditions of temperature and relative humidity. The content of meglumine still present in the tablets was determined as a function of time by an isocratic ion chromatographic method by conductivity detection, NMR or NIR.

Formaldehyde Stress Testing

In order to study the effect of meglumine on the transformation of N-(3,5-dimethoxyphenyl)-N'-(1-methylethyl)-N-[3-(1-methyl-1H-pyrazol-4-yl)quinoxalin-6-yl]ethane-1,2-diamine into 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepin in the presence of formaldehyde a solid state formaldehyde stress test was developed. In this test a solid sample (e.g. a tablet or a powder blend) was exposed to a 5% aqueous formaldehyde solution (see FIG. 1) at a temperature of 30° C. In this stress test the diffusion of formaldehyde originating from an external source and its reaction with N-(3,5-dimethoxyphenyl)-N'-(1-methylethyl)-N-[3-(1-methyl-1H-pyrazol-4-yl)quinoxalin-6-yl]ethane-1,2-diamine is simulated in a controlled, reliable and reproducible way.

The following powder blends were tested: a powder blend of 2% w/w of compound A, mannitol, microcrystalline cellulose, croscarmellose sodium and magnesium stearate; a powder blend of 2% w/w of compound A, 1% w/w of meglumine, mannitol, microcrystalline cellulose, croscarmellose sodium and magnesium stearate; a powder blend of 2% w/w of compound A, 9% w/w of meglumine, mannitol, microcrystalline cellulose, croscarmellose sodium and magnesium stearate.

Aliquots of these blends (100 mg±5 mg) were taken after 0 hour, 3 hours, 8 hours, 24 hours, 32 hours, and 48 hours, and suspended in acetonitrile/water (1/1, 4 mL). The suspension was shaken for 20 minutes and the mixture was allowed to settle down for 10 minutes. Remaining insoluble particles were removed by filtration using a syringe filter and the filtrate was analyzed by UPLC (UV detection at 256 nm using a PDA detector).

| Column | Acquity UPLC HSS T3 |
| --- | --- |
| Column length | 150 mm |
| Column diameter | 2.1 mm |
| Column temperature | 30° C. |
| Particle size | 1.8 μm |
| Flow | 0.35 mL/min |
| Injection volume | 2 μL |
| Solvent A | 10 mM NH$_4$OAc + 0.05% AcOH |
| Solvent B | Acetonitrile |

Gradient

| Time (minutes) | 0 | 12.5 | 20 | 22.5 | 23 | 27 |
| --- | --- | --- | --- | --- | --- | --- |
| % A | 85 | 40 | 0 | 0 | 85 | 85 |
| % B | 15 | 60 | 100 | 100 | 15 | 15 |

6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine (compound B) formation was determined as the area % as a function of time. The area % was calculated as the area of the 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine peak divided by the sum of the areas of all peaks above the reporting threshold of 0.05%.

When performing this formaldehyde stress test on N-(3,5-dimethoxyphenyl)-N'-(1-methylethyl)-N-[3-(1-methyl-1H-pyrazol-4-yl)quinoxalin-6-yl]ethane-1,2-diamine blends with various amounts of meglumine, the protective effect of meglumine could clearly be shown (see FIG. 2). Already the addition of 1% w/w of meglumine slowed down the degradation significantly while it was entirely inhibited in the presence of 9% w/w of meglumine.

Example 2

The following capsules were prepared (manual fill)

| Composition A | |
| --- | --- |
| N-(3,5-dimethoxyphenyl)-N'-(1-methylethyl)-N-[3-(1-methyl-1H-pyrazol-4-yl)quinoxalin-6-yl]ethane-1,2-diamine | 1 mg |
| Mannitol | 94.36 mg |
| Pregelatinized maize starch | 40.44 mg |
| Meglumine | 1.40 mg |
| Colloidal anhydrous silica | 1.40 mg |
| Magnesium stearate | 1.40 mg |
| Total weight 140 mg; filled in gelatine capsule size 4 | |
| Comparative Composition B | |
| N-(3,5-dimethoxyphenyl)-N'-(1-methylethyl)-N-[3-(1-methyl-1H-pyrazol-4-yl)quinoxalin-6-yl]ethane-1,2-diamine | 1 mg |
| Mannitol | 95.34 mg |
| Pregelatinized maize starch | 40.86 mg |
| Colloidal anhydrous silica | 1.40 mg |
| Magnesium stearate | 1.40 mg |
| Total weight 140 mg; filled in gelatin capsule size 4 | |

Detection of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine as a Function of Time in Different Conditions The capsules (open; capsule shell in the vial) were placed directly in a glass vial (at 60° C./50% RH also a closed capsule was tested). For each condition, one capsule was tested. The vials (open) were placed in a desiccator to fix the humidity using saturated salt solution and then in an oven to fix the temperature.

At appropriate time points, opened capsules were brought in a volumetric flask. N,N-Dimethylformamide was added (7 ml). The mixture was shaken for 60 minutes. Water/acetonitrile 1/1 (2 ml) was added and the mixture was shaken, and let adjust to room temperature. The mixture was diluted to volume (10 ml) with water/acetonitrile 1/1 and shaken well. The mixture was allowed to settle down for 10 minutes.

Standard stock and reference solutions were prepared from N-(3,5-dimethoxyphenyl)-N'-(1-methylethyl)-N-[3-(1-methyl-1H-pyrazol-4-yl)quinoxalin-6-yl]ethane-1,2-diamine base.

The amount of N-(3,5-dimethoxyphenyl)-N'-(1-methylethyl)-N-[3-(1-methyl-1H-pyrazol-4-yl)quinoxalin-6-yl]ethane-1,2-diamine base (compound A) and 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine base (compound B) were measured with the following operating conditions:

| UPLC System | Parameters | | | | | |
|---|---|---|---|---|---|---|
| Column | Acquity HSS T3; 2.1 × 150 mm; 1.8 µm or equivalent * | | | | | |
| Column temperature | 30° C. | | | | | |
| Autosampler temperature | 10° C. | | | | | |
| Flow rate | 0.35 ml/min | | | | | |
| Injection volume | 6.5 µl The injection volume can be adjusted as long as the qualification limits of the system are not exceeded (detector and injector) and the peak shape of the main compound is acceptable. | | | | | |
| Detection | UV detection at 256 nm Preparation and composition | | | | | |
| Mobile phase | A | 10 mM ammonium acetate (0.771 g/l) + 0.05%, v/v acetic acid in water | | | | |
| | B | Acetonitrile | | | | |
| Gradient | Solvent | Time in minutes | | | | |
| | | 0 | 12.5 | 20 | 22.5 | 23 | 27 |
| | % A | 85 | 40 | 0 | 0 | 85 | 85 |
| | % B | 15 | 60 | 100 | 100 | 15 | 15 |
| | Analytical run time is 22.5 minutes. | | | | | |

The relative retention time of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine (compound B) versus N-(3,5-dimethoxyphenyl)-N'-(1-methylethyl)-N-[3-(1-methyl-1H-pyrazol-4-yl)quinoxalin-6-yl]ethane-1,2-diamine (compound A) is 0.97. The retention time of N-(3,5-dimethoxyphenyl)-N'-(1-methylethyl)-N-[3-(1-methyl-1H-pyrazol-4-yl)quinoxalin-6-yl]ethane-1,2-diamine is 7.5 minutes.

The following conditions were tested:

For composition A: T0; 50° C./75% 3 days; 50° C./75% 7 days; 50° C./75% 14 days*; 60° C./50% 3 days; 60° C./50% 7 days; 60° C./50% 14 days*; 70° C./10% 3 days; 70° C./10% 7 days; 70° C./10% 14 days*; 70° C./75% 1 days; 70° C./75% 3 days; 70° C./75% 7 days; 70° C./75% 14 days*; 80° C./50% 1 days; 80° C./50% 3 days; 80° C./50% 7 days.

For composition B: T0; 50° C./75% 3 days; 50° C./75% 7 days; 60° C./50% 3 days; 60° C./50% 7 days; 70° C./10% 3 days; 70° C./10% 7 days; 70° C./75% 1 days; 70° C./75% 3 days; 70° C./75% 7 days; 80° C./50% 1 days; 80° C./50% 3 days; 80° C./50% 7 days. *In view of the obtained results for the 7 days storage conditions, the samples stored for 14 days were not analysed The weight/weight % of compound A and compound B were determined according to the following equation:

$$Conc_{unknown} = (Area_{unknown}/Area_{known})conc_{known}$$

wherein the unknown is either compound A or compound B and the known represents a reference standard of compound A with known concentration Results: UPLC results for Composition A

| Conditions | w/w % of compound B | w/w % of compound A |
|---|---|---|
| Initial (T0) | 0.05 | 103.0 |
| 50° C./75% 3 days | 0.06 | 101.3 |
| 50° C./75% 7 days | 0.08 | 104.0 |
| 60° C./50% 3 days | 0.59 | 101.1 |
| 60° C./50% 7 days | 1.66 | 99.5 |
| 60° C./50% 7 days-closed | 0.08 | 100.7 |
| 70° C./10% 3 days | 0.28 | 103.4 |
| 70° C./10% 7 days | 0.35 | 103.5 |

-continued

| Conditions | w/w % of compound B | w/w % of compound A |
|---|---|---|
| 70° C./75% 1 day | 0.07 | 104.6 |
| 70° C./75% 3 days | 0.16 | 87.6 |
| 70° C./75% 7 days | 0.41 | 82.7 |
| 80° C./50% 1 day | 0.08 | 102.3 |
| 80° C./50% 3 days | 0.19 | 102.0 |
| 80° C./50% 7 days | 0.56 | 97.3 |

Results: UPLC results for Comparative Composition B

| Conditions | w/w % of compound B | w/w % of compound A |
|---|---|---|
| Initial (T0) | 0.05 | 89.9 |
| 50° C./75% 3 days | 0.56 | 94.4 |
| 50° C./75% 7 days | 0.92 | 95.9 |
| 60° C./50% 3 days | 4.76 | 90.7 |
| 60° C./50% 7 days | 7.50 | 90.3 |
| 60° C./50% 7 days-closed | 0.28 | 99.9 |
| 70° C./10% 3 days | 0.79 | 94.7 |
| 70° C./10% 7 days | 1.33 | 94.5 |
| 70° C./75% 1 day | 0.44 | 94.7 |
| 70° C./75% 3 days | 0.92 | 93.6 |
| 70° C./75% 7 days | 2.74 | 92.6 |
| 80° C./50% 1 day | 0.71 | 95.4 |
| 80° C./50% 3 days | 1.63 | 94.1 |
| 80° C./50% 7 days | 3.15 | 91.8 |

The formation of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine was slowed down in Composition A compared to Comparative Composition B.

For the majority of products generated by drug degradation, reaction rates follow Arrhenius kinetics. Arrhenius kinetics is a linear dependence of the natural logarithm of the reaction rate, k, versus the reciprocal of the absolute temperature T (R is the gas constant and A is an indication of the entropy of activation for the process).

Humidity can have a significant effect on solid drug substances or drug products; even for reactions which themselves do not involve water. The humidity corrected Arrhenius equation [1] reflects both the influence of the temperature and the influence of the humidity on the kinetic of the degradant formation.

$$\ln k = \ln A - Ea/RT + B(\mathrm{RH}) \quad [1]$$

(k=reaction rate; A=an indication of the entropy of activation for the process; lnA=collision frequency; Ea=activation energy (kcal/mol); R=gas constant; T=temperature; B=humidity sensitivity factor; RH=orelative humidity)

The determination of the humidity corrected Arrhenius equation [1] for each individual degradant (via ASAPprime) allows to predict the drug product's behavior in time when placed in the different storage conditions. For each degradant, a plan of ln k vs. 1/T and RH is determined using an accelerated stability assessment program (ASAP) at extreme conditions (with temperatures from 40 up to 70° C. and RH between 10 to 75%).

The following Arrhenius parameters were used: ln A=24.8; Ea=18.8; B=0.05.

Based on the above described approach, the prediction for shelflife for Comparative Composition B was less than 1 month for a 25° C./60% RH condition. In view of this result, no further predictions were calculated.

Based on the above described approach, the prediction for shelflife for Composition A was as indicated in the below tables.

| Prediction for 25° C./60% RH condition | |
|---|---|
| Simulated package | |
| PVC blister | 2.9 years |
| Alu/Alu blister | 3.25 years |
| 100 cc/60 caps HDPE bottles | 5.6 years |
| 100 cc/60caps + 2 g desiccant HDPE bottles | 6.4 years |

| Prediction for 30° C./75% RH condition | |
|---|---|
| Simulated package | |
| PVC blister | 1.5 years |
| Alu/Alu blister | 1.8 years |
| 100 cc/60 caps HDPE bottles | 1.7 years |
| 100 cc/60caps + 2 g desiccant HDPE bottles | 2.0 years |

The invention claimed is:

1. A method of treating cancer comprising administering to a patient in need thereof a pharmaceutical composition comprising N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof; a formaldehyde scavenger; and a pharmaceutically acceptable carrier, wherein the formaldehyde scavenger is meglumine base, and wherein the cancer is bladder cancer, urothelial cancer, metastatic urothelial cancer, surgically unresectable urothelial cancer, or non-muscle-invasive bladder cancer.

2. The method according to claim 1, wherein the composition comprises from about 0.1 to about 3% w/w of the formaldehyde scavenger.

3. The method according to claim 2, wherein the composition comprises from about 0.5 to about 1.5% w/w of the formaldehyde scavenger.

4. The method according to claim 1, wherein the composition is a tablet or a capsule.

5. The method according to claim 1, wherein the composition comprises from 0-2% w/w of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, a pharmaceutically acceptable salt thereof or a solvate thereof.

6. The method according to claim 5, wherein the composition comprises from 0-0.05 w/w of 6,8-dimethoxy-4-(1-methylethyl)-1-[3-(1-methyl-1H-pyrazol-4-yl)quinoxalin-6-yl]-2,3,4,5-tetrahydro-1H-1,4-benzodiazepine, a pharmaceutically acceptable salt thereof or a solvate thereof.

7. The method according to claim 1, wherein the composition comprises from 2 mg to 6 mg base equivalent of N-(3,5-dimethoxyphenyl)-N'-(1-methylethyl)-N-[3-(1-methyl-1H-pyrazol-4-yl)quinoxalin-6-yl]ethane-1,2-diamine, a pharmaceutically acceptable salt thereof or a solvate thereof.

8. The method according to claim 1, wherein the composition comprises N-(3,5-dimethoxyphenyl)-N'-(1-methylethyl)-N-[3-(1-methyl-1H-pyrazol-4-yl)quinoxalin-6-yl]ethane-1,2-diamine base.

9. The method according to claim 2, wherein the composition comprises 3 mg of N-(3,5-dimethoxyphenyl)-N'-(1-methylethyl)-N-[3-(1-methyl-1H-pyrazol-4-yl)quinoxalin-6-yl]ethane-1,2-diamine base.

10. The method according to claim 2, wherein the composition comprises 4 mg of N-(3,5-dimethoxyphenyl)-N'-(1-methylethyl)-N-[3-(1-methyl-1H-pyrazol-4-yl)quinoxalin-6-yl]ethane-1,2-diamine base.

11. The method according to claim 2, wherein the composition comprises 5 mg of N-(3,5-dimethoxyphenyl)-N'-(1-methylethyl)-N-[3-(1-methyl-1H-pyrazol-4-yl)quinoxalin-6-yl]ethane-1,2-diamine base.

12. The method according to claim 3, wherein the composition comprises 3 mg of N-(3,5-dimethoxyphenyl)-N'-(1-methylethyl)-N-[3-(1-methyl-1H-pyrazol-4-yl)quinoxalin-6-yl]ethane-1,2-diamine base.

13. The method according to claim 3, wherein the composition comprises 4 mg of N-(3,5-dimethoxyphenyl)-N'-(1-methylethyl)-N-[3-(1-methyl-1H-pyrazol-4-yl)quinoxalin-6-yl]ethane-1,2-diamine base.

14. The method according to claim 3, wherein the composition comprises 5 mg of N-(3,5-dimethoxyphenyl)-N'-(1-methylethyl)-N-[3-(1-methyl-1H-pyrazol-4-yl)quinoxalin-6-yl]ethane-1,2-diamine base.

15. The method according to claim 6, wherein the composition comprises 3 mg of N-(3,5-dimethoxyphenyl)-N'-(1-methylethyl)-N-[3-(1-methyl-1H-pyrazol-4-yl)quinoxalin-6-yl]ethane-1,2-diamine base.

16. The method according to claim 6, wherein the composition comprises 4 mg of N-(3,5-dimethoxyphenyl)-N'-(1-methylethyl)-N-[3-(1-methyl-1H-pyrazol-4-yl)quinoxalin-6-yl]ethane-1,2-diamine base.

17. The method according to claim 6, wherein the composition comprises 5 mg of N-(3,5-dimethoxyphenyl)-N'-(1-methylethyl)-N-[3-(1-methyl-1H-pyrazol-4-yl)quinoxalin-6-yl]ethane-1,2-diamine base.

18. The method according to claim 7, wherein the composition comprises N-(3,5-dimethoxyphenyl)-N'-(1-methylethyl)-N-[3-(1-methyl-1H-pyrazol-4-yl)quinoxalin-6-yl]ethane-1,2-diamine base.

19. The method according to claim 8, wherein the composition comprises 3 mg of N-(3,5-dimethoxyphenyl)-N'-(1-methylethyl)-N-[3-(1-methyl-1H-pyrazol-4-yl)quinoxalin-6-yl]ethane-1,2-diamine base.

20. The method according to claim 8, wherein the composition comprises 4 mg of N-(3,5-dimethoxyphenyl)-N'-

(1-methylethyl)-N-[3-(1-methyl-1H-pyrazol-4-yl)quinoxalin-6-yl]ethane-1,2-diamine base.

21. The method according to claim 8, wherein the composition comprises 5 mg of N-(3,5-dimethoxyphenyl)-N'-(1-methylethyl)-N-[3-(1-methyl-1H-pyrazol-4-yl)quinoxalin-6-yl]ethane-1,2-diamine base.

22. The method according to claim 1, wherein the cancer is bladder cancer.

23. The method according to claim 1, wherein the cancer is urothelial cancer.

24. The method according to claim 1, wherein the cancer is metastatic urothelial cancer.

25. The method according to claim 1, wherein the cancer is surgically unresectable urothelial cancer.

26. The method according to claim 1, wherein the cancer is non-muscle-invasive bladder cancer.

27. The method according to claim 1, wherein the cancer is a cancer with a FGFR genomic alteration.

28. The method according to claim 1, wherein the cancer is a cancer with a FGFR translocation.

29. The method according to claim 28, wherein the translocation is a FGFR3-TACC3 translocation.

30. The method according to claim 1, wherein the cancer is a cancer with a FGFR mutation.

31. The method according to claim 30, wherein the mutation is FGFR3 R248C.

32. The method according to claim 30, wherein the mutation is FGFR3 S249C.

33. The method according to claim 2, wherein the cancer is bladder cancer.

34. The method according to claim 2, wherein the cancer is urothelial cancer.

35. The method according to claim 2, wherein the cancer is metastatic urothelial cancer.

36. The method according to claim 2, wherein the cancer is surgically unresectable urothelial cancer.

37. The method according to claim 2, wherein the cancer is non-muscle-invasive bladder cancer.

38. The method according to claim 2, wherein the cancer is a cancer with a FGFR genomic alteration.

39. The method according to claim 2, wherein the cancer is a cancer with a FGFR translocation.

40. The method according to claim 39, wherein the translocation is a FGFR3-TACC3 translocation.

41. The method according to claim 2, wherein the cancer is a cancer with a FGFR mutation.

42. The method according to claim 41, wherein the mutation is FGFR3 R248C.

43. The method according to claim 41, wherein the mutation is FGFR3 S249C.

44. The method according to claim 3, wherein the cancer is bladder cancer.

45. The method according to claim 3, wherein the cancer is urothelial cancer.

46. The method according to claim 3, wherein the cancer is metastatic urothelial cancer.

47. The method according to claim 3, wherein the cancer is surgically unresectable urothelial cancer.

48. The method according to claim 3, wherein the cancer is non-muscle-invasive bladder cancer.

49. The method according to claim 3, wherein the cancer is a cancer with a FGFR genomic alteration.

50. The method according to claim 3, wherein the cancer is a cancer with a FGFR translocation.

51. The method according to claim 50, wherein the translocation is a FGFR3-TACC3 translocation.

52. The method according to claim 3, wherein the cancer is a cancer with a FGFR mutation.

53. The method according to claim 52, wherein the mutation is FGFR3 R248C.

54. The method according to claim 52, wherein the mutation is FGFR3 S249C.

55. The method according to claim 6, wherein the cancer is bladder cancer.

56. The method according to claim 6, wherein the cancer is urothelial cancer.

57. The method according to claim 6, wherein the cancer is metastatic urothelial cancer.

58. The method according to claim 6, wherein the cancer is surgically unresectable urothelial cancer.

59. The method according to claim 6, wherein the cancer is non-muscle-invasive bladder cancer.

60. The method according to claim 6, wherein the cancer is a cancer with a FGFR genomic alteration.

61. The method according to claim 6, wherein the cancer is a cancer with a FGFR translocation.

62. The method according to claim 61, wherein the translocation is a FGFR3-TACC3 translocation.

63. The method according to claim 6, wherein the cancer is a cancer with a FGFR mutation.

64. The method according to claim 63, wherein the mutation is FGFR3 R248C.

65. The method according to claim 63, wherein the mutation is FGFR3 S249C.

66. The method according to claim 9, wherein the cancer is bladder cancer.

67. The method according to claim 10, wherein the cancer is bladder cancer.

68. The method according to claim 11, wherein the cancer is bladder cancer.

69. The method according to claim 9, wherein the cancer is urothelial cancer.

70. The method according to claim 10, wherein the cancer is urothelial cancer.

71. The method according to claim 11, wherein the cancer is urothelial cancer.

72. The method according to claim 9, wherein the cancer is metastatic urothelial cancer.

73. The method according to claim 10, wherein the cancer is metastatic urothelial cancer.

74. The method according to claim 11, wherein the cancer is metastatic urothelial cancer.

75. The method according to claim 9, wherein the cancer is surgically unresectable urothelial cancer.

76. The method according to claim 10, wherein the cancer is surgically unresectable urothelial cancer.

77. The method according to claim 11, wherein the cancer is surgically unresectable urothelial cancer.

78. The method according to claim 9, wherein the cancer is non-muscle-invasive bladder cancer.

79. The method according to claim 10, wherein the cancer is non-muscle-invasive bladder cancer.

80. The method according to claim 11, wherein the cancer is non-muscle-invasive bladder cancer.

81. The method according to claim 26, wherein the cancer is a cancer with a FGFR genomic alteration.

82. The method according to claim 26, wherein the cancer is a cancer with a FGFR translocation.

83. The method according to claim 82, wherein the translocation is a FGFR3-TACC3 translocation.

84. The method according to claim 26, wherein the cancer is a cancer with a FGFR mutation.

85. The method according to claim 84, wherein the mutation is FGFR3 R248C.

86. The method according to claim 84, wherein the mutation is FGFR3 S249C.

87. The method according to claim 26, wherein the composition comprises N-(3,5-dimethoxyphenyl)-N'-(1-methylethyl)-N-[3-(1-methyl-1H-pyrazol-4-yl)quinoxalin-6-yl]ethane-1,2-diamine base.

* * * * *